US012792879B2

(12) United States Patent
Jain et al.

(10) Patent No.: US 12,792,879 B2
(45) Date of Patent: Nov. 10, 2026

(54) SYSTEMS AND METHODS TO ANALYZE IMAGES OF LATERAL FLOW ASSAYS

(71) Applicant: Abbott Rapid Diagnostics International Unlimited Company, Dublin (IE)

(72) Inventors: Jinesh Jitendrakumar Jain, Cupertino, CA (US); Bart Heerkens, Moedling (AT); Shimin Li, Acton, MA (US); Angela Zhang, Stow, MA (US); John Schullian, Cary, IL (US); Shailaja Tulugu, South Barrington, IL (US)

(73) Assignee: Abbott Rapid Diagnostics International Unlimited Company, Dublin (IE)

( * ) Notice: Subject to any disclaimer, the term of this patent is extended or adjusted under 35 U.S.C. 154(b) by 849 days.

(21) Appl. No.: 17/844,397

(22) Filed: Jun. 20, 2022

(65) Prior Publication Data

US 2022/0405551 A1 Dec. 22, 2022

Related U.S. Application Data

(60) Provisional application No. 63/266,968, filed on Jan. 20, 2022, provisional application No. 63/213,049, filed on Jun. 21, 2021.

(51) Int. Cl.

*G06N 3/045* (2023.01)
*G01N 21/77* (2006.01)
*G01N 33/543* (2006.01)

(52) U.S. Cl.

CPC ....... *G06N 3/045* (2023.01); *G01N 33/54388* (2021.08); *G01N 2021/7759* (2013.01); *G01N 2021/7763* (2013.01)

(58) Field of Classification Search

CPC ............... B01D 53/9495; F01N 13/107; F01N 2430/06; F01N 2610/03; F02B 37/00;

(Continued)

(56) References Cited

U.S. PATENT DOCUMENTS

| | | | |
|---|---|---|---|
| 7,267,799 | B1 | 9/2007 | Borich et al. |
| 7,313,257 | B2 | 12/2007 | Roman |

(Continued)

FOREIGN PATENT DOCUMENTS

| | | |
|---|---|---|
| AU | 2020217956 | 8/2021 |
| CN | 102008294 | 4/2011 |

(Continued)

OTHER PUBLICATIONS

Lee et al., "Sample-to-answer platform for the clinical evaluation of COVID-19 using a deep learning-assisted smartphone-based assay," published Apr. 24, 2023, retrieved from https://doi.org/10.1038/s41467-023-38104-5, 11 pages.

*Primary Examiner* — Jennifer Wecker
*Assistant Examiner* — Jonathan Bortoli
(74) *Attorney, Agent, or Firm* — Hanley, Flight & Zimmerman, LLC

(57) ABSTRACT

Systems and methods to analyzes images of lateral flow assays are disclosed herein. An example image analysis system includes processor circuitry to (a) determine whether a format of an image of a lateral flow assay device satisfies a format threshold, (b) in response to determining the format of the image satisfies the format threshold, determine whether the lateral flow assay device in the image is authentic, (c) in response to determining the lateral flow assay device is authentic, determine whether a position of the lateral flow assay device in the image satisfies a position threshold, (d) in response to determining the position of the lateral flow assay device satisfies the position threshold, (Continued)

analyze the image to determine the result of the diagnostic test, and (e) abort the sequence of the operations during performance of the sequence of operations at the time any one of operations fails.

9 Claims, 22 Drawing Sheets

(58) Field of Classification Search
CPC .. F02B 37/025; F02D 41/0065; F02D 41/008; F02D 41/0275; F02D 41/405; F02D 21/08; F02M 26/15; F02M 26/05; F02M 26/57; Y02T 10/12; Y02T 10/40; A61M 16/161; A61M 2021/0011; A61M 2021/0016; A61M 2021/0022; A61M 2021/0027; A61M 2021/0044; A61M 2021/0066; A61M 21/0094; A61M 21/02; A61M 2205/0205; A61M 2205/0238; A61M 2205/3303; A61M 2205/3368; A61M 2205/3553; A61M 2205/3561; A61M 2205/3584; A61M 2205/3592; A61M 2205/42; A61M 2205/50; A61M 2205/505; A61M 2205/6018; A61M 2205/6054; A61M 2205/7509; A61M 2205/7518; A61M 2205/7545; A61M 2230/04; A61M 2230/50; A61M 2230/63; A61N 2005/0626; A61N 5/0618; F24F 11/0008; F24F 2120/10; F24F 3/12; F24F 8/50; G05B 15/02; G05B 2219/2642; G08C 23/04; G16H 20/30; G16H 20/70; G16H 40/63; G16H 40/67; H04L 12/282; H04L 12/2829; H05B 47/10; H05B 47/11; Y02A 90/10; Y02B 20/40; G01N 2021/7759; G01N 2021/7763; G01N 21/78; G01N 21/8483; G01N 33/54388; G06N 20/00; G06N 3/045; G06N 3/0464; G06N 3/09; G06N 3/096; G06T 2207/20084; G06T 2207/30168; G06T 7/0002
See application file for complete search history.

(56) References Cited

U.S. PATENT DOCUMENTS 7,459,314 B2 12/2008 Guo et al.
8,145,431 B2 3/2012 Kloepfer et al.
8,257,980 B2 9/2012 Schalkhammer
8,411,916 B2 4/2013 Hsieh et al.
8,583,379 B2 11/2013 Li et al.
8,638,441 B2 1/2014 Egan et al.
8,655,009 B2 2/2014 Chen et al.
8,792,693 B2 7/2014 Satish et al.
9,063,091 B2 6/2015 Tsai et al.
9,185,200 B2 11/2015 Cunningham
9,410,827 B2 8/2016 Ghazizadeh
9,489,703 B2 11/2016 Kauniskangas et al.
9,658,217 B2 5/2017 Chen et al.
9,686,395 B2 6/2017 Erickson et al.
9,778,200 B2 10/2017 Tsai et al.
9,787,815 B2 10/2017 Erickson et al.
9,886,750 B2 2/2018 Price et al.
9,903,857 B2 2/2018 Polwart et al.
10,054,584 B2 8/2018 Ehrenkranz et al.
10,055,837 B2 8/2018 Lee et al.
10,067,125 B2 9/2018 Mamenta
10,126,539 B2 11/2018 Fletcher et al.
10,132,743 B2 11/2018 Lenigk et al.
10,132,794 B2 11/2018 Chou et al.
10,132,802 B2 11/2018 Ehrenkranz
10,146,909 B2 12/2018 Dimov et al.
10,267,742 B2 4/2019 Khan
10,340,032 B2 7/2019 Ramsey et al.
10,345,240 B2 7/2019 Chan et al.
10,352,920 B2 7/2019 Ehrenkranz
10,473,659 B2 11/2019 Pulitzer et al.
10,498,936 B2 12/2019 Ehrenkranz
10,527,555 B2 1/2020 Pulitzer et al.
10,571,395 B2 2/2020 Karlovac et al.
10,605,741 B2 3/2020 Lu et al.
10,663,466 B2 5/2020 Ozcan et al.
10,753,861 B2 8/2020 Zaccari et al.
10,753,932 B2 8/2020 Hopper
10,789,710 B2 9/2020 Satish et al.
10,818,379 B2 10/2020 Krishnan et al.
10,859,560 B2 12/2020 Sumathipala et al.
10,902,951 B2 1/2021 Pulitzer et al.
10,972,641 B2 4/2021 Chou et al.
11,054,410 B2 7/2021 Chen et al.
11,105,801 B2 8/2021 Gordon
11,112,406 B2 9/2021 Pulitzer et al.
2005/0203353 A1 9/2005 Ma et al.
2010/0110439 A1 5/2010 Gruler et al.
2010/0167283 A1 7/2010 Horgan et al.
2012/0075626 A1 3/2012 Geva et al.
2014/0227681 A1 8/2014 Fleming et al.
2014/0242612 A1 8/2014 Wang et al.
2015/0177147 A1 6/2015 Mangan et al.
2016/0188937 A1 6/2016 Tyrrell et al.
2016/0274104 A1 9/2016 Aminoff et al.
2017/0055111 A1 2/2017 Nazareth et al.
2018/0196037 A1 7/2018 Polwart et al.
2018/0199827 A1 7/2018 Satish et al.
2019/0079084 A1 3/2019 Gordon
2019/0111425 A1 4/2019 Wronko
2019/0187140 A1 6/2019 Kamei et al.
2019/0271695 A1 9/2019 Egan et al.
2019/0346369 A1 11/2019 Ozcan et al.
2019/0384890 A1 12/2019 Pulitzer et al.
2020/0011801 A1* 1/2020 Hunter .............. G01N 21/6456
2020/0033579 A1 1/2020 Chou et al.
2020/0080942 A1 3/2020 Chen et al.
2020/0183137 A1 6/2020 Hu et al.
2020/0249229 A1 8/2020 Bhatia et al.
2020/0254445 A1 8/2020 Chou et al.
2020/0256856 A1 8/2020 Chou et al.
2020/0298240 A1 9/2020 Oshinski et al.
2020/0309769 A1 10/2020 Heron et al.
2020/0333322 A1 10/2020 Chou et al.
2020/0340988 A1 10/2020 Ehrenkranz
2020/0363408 A1 11/2020 Chou et al.
2020/0371031 A1 11/2020 Kohlmann et al.
2020/0376491 A1 12/2020 Deng et al.
2020/0393359 A1 12/2020 Ozcan et al.
2021/0007643 A1 1/2021 Lamrani et al.
2021/0033599 A1 2/2021 Kiyuna et al.
2021/0089814 A1 3/2021 Lopes et al.
2021/0129133 A1 5/2021 Ohta et al.
2021/0129136 A1 5/2021 Neuman et al.
2021/0129143 A1 5/2021 Yoon et al.
2021/0132035 A1 5/2021 Adelman
2021/0140957 A1 5/2021 Chou et al.
2021/0156771 A1 5/2021 Chou et al.
2021/0164975 A1 6/2021 Sarhan et al.
2021/0172945 A1 6/2021 Armbruster et al.
2021/0180110 A1 6/2021 Shachar et al.
2021/0215666 A1 7/2021 Kotanko et al.
2021/0231574 A1 7/2021 Wang et al.
2021/0263018 A1 8/2021 Taran
2021/0264604 A1 8/2021 Divaraniya et al.
2021/0374959 A1* 12/2021 Yaghoubi .............. G06T 7/0014
2022/0215934 A1 7/2022 Adiri et al.

FOREIGN PATENT DOCUMENTS

CN 103477197 12/2013
CN 203909044 10/2014
CN 104914239 9/2015
CN 106198538 12/2016

(56) References Cited

FOREIGN PATENT DOCUMENTS

| | | |
|---|---|---|
| CN | 106680478 | 5/2017 |
| CN | 106841590 | 6/2017 |
| CN | 207366570 | 5/2018 |
| CN | 207408411 | 5/2018 |
| CN | 107121542 | 8/2018 |
| CN | 108519480 | 9/2018 |
| CN | 108562741 | 9/2018 |
| CN | 109187946 | 1/2019 |
| CN | 109358190 | 2/2019 |
| CN | 107255712 | 8/2019 |
| CN | 110220891 | 9/2019 |
| CN | 110456050 | 11/2019 |
| CN | 110567929 | 12/2019 |
| CN | 110580952 | 12/2019 |
| CN | 110580953 | 12/2019 |
| CN | 110887960 | 3/2020 |
| CN | 111033563 | 4/2020 |
| CN | 111220801 | 6/2020 |
| CN | 111247404 | 6/2020 |
| CN | 111247422 | 6/2020 |
| CN | 111751523 | 10/2020 |
| CN | 112213482 | 1/2021 |
| CN | 112326959 | 2/2021 |
| CN | 112394165 | 2/2021 |
| DE | 102008026803 | 12/2009 |
| DE | 202021102008 | 7/2021 |
| EP | 2746750 | 6/2014 |
| EP | 3442415 | 2/2019 |
| EP | 3311163 | 8/2020 |
| EP | 3608668 | 1/2021 |
| EP | 3791167 | 3/2021 |
| EP | 3803384 | 4/2021 |
| EP | 3865862 | 8/2021 |
| IN | 201841037397 | 4/2020 |
| IN | 202031023859 | 6/2021 |
| JP | 2002101037 | 4/2002 |
| JP | 2007101482 | 4/2007 |
| JP | 2008046099 | 2/2008 |
| JP | 2019191055 | 10/2019 |
| JP | 2019196987 | 11/2019 |
| KR | 470398 | 12/2013 |
| KR | 20150062283 | 6/2015 |
| KR | 1634541 | 7/2016 |
| KR | 2018064705 | 6/2018 |
| KR | 2034352 | 10/2019 |
| KR | 2119578 | 6/2020 |
| KR | 2020121808 | 10/2020 |
| KR | 2269429 | 6/2021 |
| SG | 11201801134 | 3/2016 |
| SG | 11201802055 | 4/2018 |
| WO | WO2010095394 | 8/2010 |
| WO | WO2013120191 | 8/2013 |
| WO | WO2014077783 | 5/2014 |
| WO | WO2016154613 | 9/2016 |
| WO | WO2017223159 | 12/2017 |
| WO | WO2018026725 | 2/2018 |
| WO | WO2018194525 | 10/2018 |
| WO | WO2019246361 | 12/2019 |
| WO | WO2020016616 | 1/2020 |
| WO | WO2020082029 | 4/2020 |
| WO | WO2020128146 | 6/2020 |
| WO | WO2020163658 | 8/2020 |
| WO | WO2020198511 | 10/2020 |
| WO | WO2020218913 | 10/2020 |
| WO | WO2020231159 | 11/2020 |
| WO | WO2020242993 | 12/2020 |
| WO | WO2021004564 | 1/2021 |
| WO | WO2021011944 | 1/2021 |
| WO | WO2021013392 | 1/2021 |
| WO | WO2021045475 | 3/2021 |
| WO | WO2021051045 | 3/2021 |
| WO | WO2021092595 | 5/2021 |
| WO | WO2021102741 | 6/2021 |
| WO | WO2021140199 | 7/2021 |
| WO | WO2021150812 | 7/2021 |
| WO | WO2022010997 | 1/2022 |
| WO | WO2022108711 | 5/2022 |
| WO | WO2022150857 | 7/2022 |

* cited by examiner

SYSTEMS AND METHODS TO ANALYZE IMAGES OF LATERAL FLOW ASSAYS

RELATED APPLICATIONS

This patent claims the benefit under 35 U.S.C. § 119(e) to U.S. Provisional Application No. 63/213,049, titled "SYSTEMS AND METHODS TO ANALYZE IMAGES OF LATERAL FLOW ASSAYS," filed Jun. 21, 2021, and U.S. Provisional Application No. 63/266,968, titled "SYSTEMS AND METHODS TO ANALYZE IMAGES OF LATERAL FLOW ASSAYS," filed Jan. 20, 2022, both of which are hereby incorporated by this reference in their entireties.

FIELD OF THE DISCLOSURE

This disclosure relates generally to lateral flow assays and, more particularly, to systems and methods to analyze images of lateral flow assays.

BACKGROUND

A lateral flow assay (LFA) is a device that is capable of detecting a condition, disease, etc., in a human or animal based on a sample (e.g., a blood sample, a saliva sample, a urine sample, etc.) from the human or animal. LFAs have been used to detect the presence of a target analyte to determine pregnancy, determine presence of a virus, such as COVID-19, HIV, Ebola, etc., presence of different toxins, etc.

BRIEF DESCRIPTION OF THE DRAWINGS

The figures are not to scale. In general, the same reference numbers will be used throughout the drawing(s) and accompanying written description to refer to the same or like parts.

Figure 1:
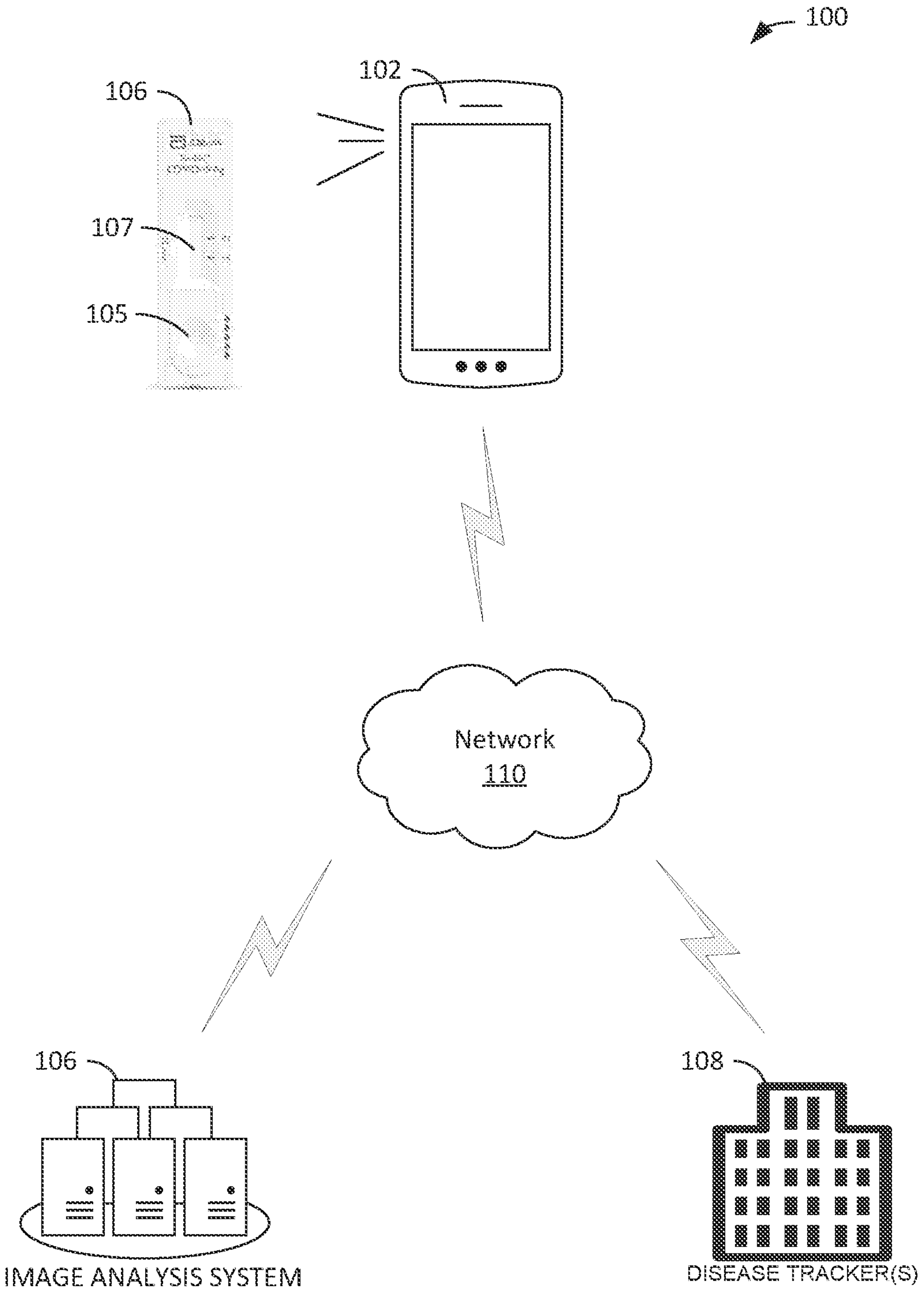
FIG. 1 illustrates an example environment including an example user electronic device and an example image analysis system that can analyze an image of a lateral flow assay (LFA) taken by the example user device.

Unless specifically stated otherwise, descriptors such as "first," "second," "third," etc., are used herein without imputing or otherwise indicating any meaning of priority, physical order, arrangement in a list, and/or ordering in any way, but are merely used as labels and/or arbitrary names to distinguish elements for ease of understanding the disclosed examples. In some examples, the descriptor "first" may be used to refer to an element in the detailed description, while the same element may be referred to in a claim with a different descriptor such as "second" or "third." In such instances, it should be understood that such descriptors are used merely for identifying those elements distinctly that might, for example, otherwise share a same name. As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events. As used herein, "processor circuitry" is defined to include (i) one or more special purpose electrical circuits structured to perform specific operation(s) and including one or more semiconductor-based logic devices (e.g., electrical hardware implemented by one or more transistors), and/or (ii) one or more general purpose semiconductor-based electrical circuits programmed with instructions to perform specific operations and including one or more semiconductor-based logic devices (e.g., electrical hardware implemented by one or more transistors). Examples of processor circuitry include programmed microprocessors, Field Programmable Gate Arrays (FPGAs) that may instantiate instructions, Central Processor Units (CPUs), Graphics Processor Units (GPUs), Digital Signal Processors (DSPs), XPUs, or microcontrollers and integrated circuits such as Application Specific Integrated Circuits (ASICs). For example, an XPU may be implemented by a heterogeneous computing system including multiple types of processor circuitry (e.g., one or more FPGAs, one or more CPUs, one or more GPUs, one or more DSPs, etc., and/or a combination thereof) and application programming interface(s) (API(s)) that may assign computing task(s) to whichever one(s) of the multiple types of the processing circuitry is/are best suited to execute the computing task(s).

DETAILED DESCRIPTION

A lateral flow assay (LFA), sometimes referred to as a test strip, test kit, or a rapid test, is a diagnostic test strip that includes a first region to obtain a sample (e.g., blood, urine, saliva, etc.) and a second region that changes color when a target analyte corresponding to a particular disease or condition is present in the sample. For example, a user may apply a sample to a sample pad of a test strip. Once applied, the sample migrates along the test strip to a conjugate pad that contains conjugates (e.g., detectable labels, tags, linkers, antibodies, antigens, etc.) specific to the target analyte. If the sample includes the target analyte, a chemical reaction occurs on the conjugate pad to bind the target analyte with the conjugates. The test strip also includes a test line that contains immobilized antibodies and/or antigens specific to the target analyte, which bind the first set of conjugate molecules (e.g., probe molecules) from the conjugate pad. For example, if the analyte of interest is an antibody, the positive test area includes immobilized antigen. If the analyte of interest is an antigen, the positive test area includes immobilized antibody. The labeled substance or conjugate includes a first binding component that is able to bind the analyte of interest and a second visualization component. Accordingly, when the sample (e.g., including the bounded target analyte) flows to a test zone (e.g., a reaction zone), the antibodies or antigens of the test line bind to the bounded target analyte, thereby immobilizing the target analyte. In some test strips, the immobilized target analytes result in one or more visual indicators or output that represent whether the target analyte was present or absent in the sample. A user can view the visual indicator(s)/output(s) and determine whether the sample was positive, negative, invalid, etc. Example LFAs that can be implemented in connection with the examples disclosed herein are described in U.S. Pat. No. 5,622,871, titled "Capillary Immunoassay and Device Thereof Comprising Mobilizable Particulate Labelled Reagents," filed Jul. 15, 1993; U.S. Pat. No. 6,485,982, titled "Test Device and Method for Colored Particle Immunoassay," filed Jun. 6, 1995; U.S. Pat. No. 6,187,598, titled "Capillary Immunoassay and Device Thereof Comprising Mobilizable Particulate Labelled Reagents," filed Jun. 7, 1995; U.S. Pat. No. 6,565,808, titled "Line Test Device and Methods of Use," filed May 18, 2001; U.S. Pat. No. 8,828,739, titled "Lateral Flow Immunoassay Controls," filed May 25, 2012; and U.S. application Ser. No. 10/717,082, titled "Lateral Flow Immunoassay Devices for Testing Saliva and Other Liquid Samples and Methods of Use of Same," filed Nov. 19, 2003, all of which are incorporated herein by this reference in their entireties.

"Target analyte", "analyte" or "analyte of interest" refers to the compound or the composition to be detected or measured from the sample, which has at least one epitope or binding site. The analyte can be any substance for which there exists a naturally occurring analyte-specific binding member or for which an analyte-specific binding member can be prepared. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), and/or metabolites of or antibodies to any of the above substances. The term "analyte" also includes any antigenic substances, haptens, antibodies, macromolecules, and/or combinations thereof.

"Label" refers to any substance which is capable of producing a signal that is detectable by visual and/or instrumental means. Various labels suitable for use in examples disclosed herein include labels that produce signals through chemical and/or physical means. Examples include enzymes and substrates, chromagens, fluorescent compounds, chemiluminescent compounds, colored or colorable organic polymer latex particles, liposomes, and/or other vesicles containing directly visible substances. In some examples, radioactive labels, colloidal metallic particles, and/or colloidal non-metallic particles are employed. In some examples, labels include colloidal gold and latex particles.

"Labeled substance" or "conjugate" refers to a substance that includes a detectable label attached to a specific binding member. The attachment may be covalent or non-covalent binding and may include nucleic acid hybridization. The label allows the labeled substance to produce a detectable signal that is directly or indirectly related to the amount of analyte in a test sample. The specific binding member component of the labeled substance is selected to bind directly or indirectly to the analyte.

"Specific binding member" refers to a member of a specific binding pair (e.g., two different molecules wherein one of the molecules specifically binds to the second molecule through chemical or physical means). If the specific binding member is an immunoreactant it can be, for example, an antibody, antigen, hapten, or complex thereof, and if an antibody is used, it can be a monoclonal or polyclonal antibody, a recombinant protein or antibody, a chimeric antibody, a mixture(s) or fragment(s) thereof, as well as a mixture of an antibody and other specific binding members. Specific examples of specific binding members include biotin and avidin, an antibody and its corresponding antigen (both having no relation to a sample to be assayed), a single stranded nucleic acid and its complement, and the like.

The terms "test strip," "lateral flow assay" (or "LFA"), or "LFA device" are used interchangeably herein. A test strip can include one or more bibulous or non-bibulous materials. If a test strip includes more than one material, the one or more materials are preferably in fluid communication. One material of a test strip may be overlaid on another material of the test strip, such as for example, filter paper overlaid on nitrocellulose. Additionally or alternatively, a test strip may include a region including one or more materials (e.g., media) followed by a region including one or more different materials. In this case, the regions are in fluid communication and may or may not partially overlap one another. Suitable materials for test strips include, but are not limited to, materials derived from cellulose, such as filter paper, chromatographic paper, nitrocellulose, and cellulose acetate, as well as materials made of glass fibers, nylon, dacron, polyvinyl chloride (PVC), polyacrylamide, cross-linked dextran, agarose, polyacrylate, ceramic materials, and the like. The material or materials of the test strip may optionally be treated to modify their capillary flow characteristics or the characteristics of the applied sample. For example, the sample application region of the test strip may be treated with buffers to correct the pH or specific gravity of an applied urine sample, to ensure optimal test conditions.

In some conventional LFAs, the visual indicators or outputs in the test region appear as one or more colored features, such as a line or marking. However, these features often have faint color changes that result in an increase in user error when visually reading the features with the human eye. For example, although an LFA may output a color corresponding to a positive result, if the color is faint and/or the lighting conditions are poor, a user may interpret the test as negative. Also, users commonly make mistakes when entering their results into a program, such as an application on a smartphone or computer.

Disclosed herein are example systems and methods to analyze an image of a LFA and automatically determine the result of the LFA test based on the image analysis. The examples disclosed herein ensure accurate result determination and produce better results than current systems. The examples disclosed herein also reduce human error when interpreting and/or inputting results.

Disclosed herein is an example image analysis system that can analyze an image of a LFA taken by a user's electronic device (e.g., a smartphone). For example, a user may perform the test with the LFA and take a picture/image (e.g., with a camera for the electronic device) of the LFA. The electronic device transmits the image to the image analysis system. The image analysis system analyzes the image using one or more operations to determine the result of the test. In some examples, the image analysis system transmits the result to the electronic device to be displayed to the user.

In some examples, the image analysis system transmits the result to one or more disease tracker entities, such as the Centers for Disease Control and Prevention (CDC). The disease tracker entities may monitor the spread of an infectious disease or virus. In some examples, the image analysis system does not report the result back to the electronic device (i.e., to the user). Instead, the results of tests are only sent to the disease trackers for monitoring. Therefore, in some examples, the example techniques disclosed herein are for epidemiological purposes (and not diagnostic purposes). In other examples, the results are provided to the user in addition to reporting to a government agency or other third party.

In some examples, the image analysis process uses one or more artificial intelligence models. Artificial intelligence (AI), including machine learning (ML), deep learning (DL), and/or other artificial machine-driven logic, enables machines (e.g., computers, logic circuits, etc.) to use a model to process input data to generate an output based on patterns and/or associations previously learned by the model via a training process. For instance, the model may be trained with data to recognize patterns and/or associations and follow such patterns and/or associations when processing input data such that other input(s) result in output(s) consistent with the recognized patterns and/or associations.

Many different types of machine learning models and/or machine learning architectures exist. In examples disclosed herein, a Convolutional Neural Network (CNN) model is used. Using a CNN model enables accurate image analysis. Examples of CNN models or architectures that can be implemented herein include Generative Adversarial Network, LeNet, ResNet (also referred to as Residual Networks), EfficientNet, GoogleNet (also referred to as the Inception Network), VGG (e.g., VGGNET 16), DenseNet, and/or AlexNet. However, other types of machine learning models could additionally or alternatively be used, such as Support Vector Machine (SVM), Deep Neural Network (DNN), Recurrent Neural Network (RNN), Long Short Term Memory (LSTM), and Gated Recurrent Unit (GRU).

In general, implementing a ML/AI system involves two phases, a learning/training phase and an inference phase. In the learning/training phase, a training algorithm is used to train a model to operate in accordance with patterns and/or associations based on, for example, training data. In general, the model includes internal parameters that guide how input data is transformed into output data, such as through a series of nodes and connections within the model to transform input data into output data. Additionally, hyperparameters are used as part of the training process to control how the learning is performed (e.g., a learning rate, a number of layers to be used in the machine learning model, etc.). Hyperparameters are defined to be training parameters that are determined prior to initiating the training process.

Different types of training may be performed based on the type of ML/AI model and/or the expected output. For example, supervised training uses inputs and corresponding expected (e.g., labeled) outputs to select parameters (e.g., by iterating over combinations of select parameters) for the ML/AI model that reduce model error. As used herein, labelling refers to an expected output of the machine learning model (e.g., a classification, an expected output value, etc.). Alternatively, unsupervised training (e.g., used in deep learning, a subset of machine learning, etc.) involves inferring patterns from inputs to select parameters for the ML/AI model (e.g., without the benefit of expected (e.g., labeled) outputs).

In some examples disclosed herein, ML/AI models are trained using stochastic gradient descent. However, any other training algorithm may additionally or alternatively be used. In some examples disclosed herein, training is performed until an acceptable error is achieved. In some examples disclosed herein, training is performed locally (e.g., at the image analysis system) and/or remotely (e.g., at an off-site training facility). Training is performed using hyperparameters that control how the learning is performed (e.g., a learning rate, a number of layers to be used in the machine learning model, etc.). In some examples re-training may be performed. Such re-training may be performed in response to a number of errors in image capture and/or a number of invalid test results.

Training is performed using training data. In examples disclosed herein, the training data originates from publicly available and/or locally generated images of test strips. Because supervised training is used, the training data is labeled.

Once training is complete, the model is deployed for use as an executable construct that processes an input and provides an output based on the network of nodes and connections defined in the model. The model is stored at the image analysis system. The model may then be executed by the processor circuitry of the image analysis system.

Once trained, the deployed model may be operated in an inference phase to process data. In the inference phase, data to be analyzed (e.g., live data) is input to the model, and the model executes to create an output. This inference phase can be thought of as the AI "thinking" to generate the output based on what it learned from the training (e.g., by executing the model to apply the learned patterns and/or associations to the live data). In some examples, input data undergoes pre-processing before being used as an input to the machine learning model. Moreover, in some examples, the output data may undergo post-processing after it is generated by the AI model to transform the output into a useful result (e.g., a display of data, an instruction to be executed by a machine, etc.).

In some examples, output of the deployed model may be captured and provided as feedback. By analyzing the feedback, an accuracy of the deployed model can be determined. If the feedback indicates that the accuracy of the deployed model is less than a threshold or other criterion, training of an updated model can be triggered using the feedback and an updated training data set, hyperparameters, etc., to generate an updated, deployed model.

FIG. 1 illustrates an example system or environment 100 including an example user electronic device 102 and an example image analysis system 104 that can analyze and interpret the results of an image of a lateral flow assay (LFA) 106, referred to herein as a test strip 106. For example, a user can perform a test with the example test strip 106. After the test is performed, the user can use the electronic device 102 to obtain an image or picture of the test strip 106. The electronic device 102 transmits the image to the image analysis system 104. The image analysis system 104 analyzes the image to determine the results of the test, such as positive, negative, invalid, etc. In some examples, the image analysis system 104 transmits the result to one or more disease tracker(s) 108. The disease tracker(s) 108 can include an entity that collects and monitors the spread of a disease associated with the test strip 106. For example, the disease tracker(s) 108 can include a government agency like the Centers for Disease Control and Prevention (CDC). In other examples, the disease trackers 108 can be a private organization or company. Additionally or alternatively, in some examples, the image analysis system 104 sends results of the test to the electronic device 102, which can be displayed to the user (e.g., via an application on the electronic device 102). In the illustrated example, the electronic device 102, the image analysis system 104, and the disease trackers 108 communicate via a network 110, such as, for example, the Internet.

The example test strip 106 implements a diagnostic test to test a biological sample (e.g., blood, saliva, urine) from the user for a presence or an absence of a target analyte. In the illustrated example, the test strip 106 has a sample region 105 to receive a biological sample. The test strip 106 also has a test region 107. The test region 107 generates one or more visual outputs or indicators based on the presence or absence of one or more target analytes in the sample, thereby representing the result of the diagnostic test. The visual indicators can include lines, dots, patterns, etc. In some examples, the test strip 106 is configured to test for multiple target analytes (e.g., multiple viruses) at the same time. In such an example, the test region 107 can generate multiple visual outputs (e.g., multiple lines) corresponding to the target analytes. In other examples, the test strip 106 is only configured to test for one target analyte. In this example, the test region includes a test line (T) area and a control line (C) area. If the target analyte is present, a colored line (e.g., a blue line, a red line, etc.) appears at the test line (T) area of the test region 107. The control line (C) area generates another line to ensure the test strip 106 is operating correctly. Generally, a person can view the lines (or lack of one or more of the lines) and determine the result of the test (e.g., by comparing the line scheme to one or more known line schemes). However, users may make mistakes when interpreting the presence or absence of the lines and/or make mistakes when entering the result into an electronic device. Therefore, the image analysis system 104 reduces errors in the process by automatically analyzing the image to determine the result. The subjectivity in human interpretation is removed, and the image analysis system 104 produces objective and accurate results.

The electronic device 102 can be implemented by any type of electronic device. In the illustrated example, the electronic device 102 is implemented as a smartphone. However, in other examples, the electronic device 102 can be implemented as any other type of mobile or non-mobile electronic device, such as a person computer, a laptop, a tablet, etc. In some examples, the electronic device 102 uses an application (e.g., a downloaded application also known as an app) to communicate with the image analysis system 104. In some examples, the application is downloaded from the image analysis system 104 or another entity, such as, for example, the Apple App Store or the Google Play Store. Thus, the example application disclosed herein can utilize different operating systems. While in the illustrated example only one electronic device 102 is depicted, it understood that the example environment 100 can include any number of electronic devices. Therefore, multiple electronic devices operated by multiple users can connect with the image analysis system 104.

In the illustrated example, the image analysis system 104 is remote from the electronic device 102 (e.g., in a cloud-based computing system). Therefore, the electronic device 102 does not perform the image analysis. Instead, the electronic device 102 obtains the image and transmits the image to the image analysis system 104. In some examples, this reduces the processing power required by the electronic device 102. In some examples, the image analysis system 104 is owned, controlled, and/or otherwise operated by the manufacturer of the test strip 106. In other examples, the image analysis system 104 can be controlled or operated by a testing entity. For example, the image analysis system 104 can be provided by a hospital or medical facility. In some examples, the image analysis system 104 operates via an edge server in an edge computing environment. For example, the image analysis system 104 may be supported on an edge server hosted by a telecommunications company, a hospital or other medical facility, a government, etc. In other examples, the image analysis system 104 can be integral to the electronic device 102. For example, one or more operations disclosed herein in connection with the image analysis system 104 can be performed by software on the electronic device 102. In such examples, the image analysis system 104 may be incorporated into the app downloaded by the electronic device 102. Such examples facilitate real time determination and reporting of test results.

Figure 2:
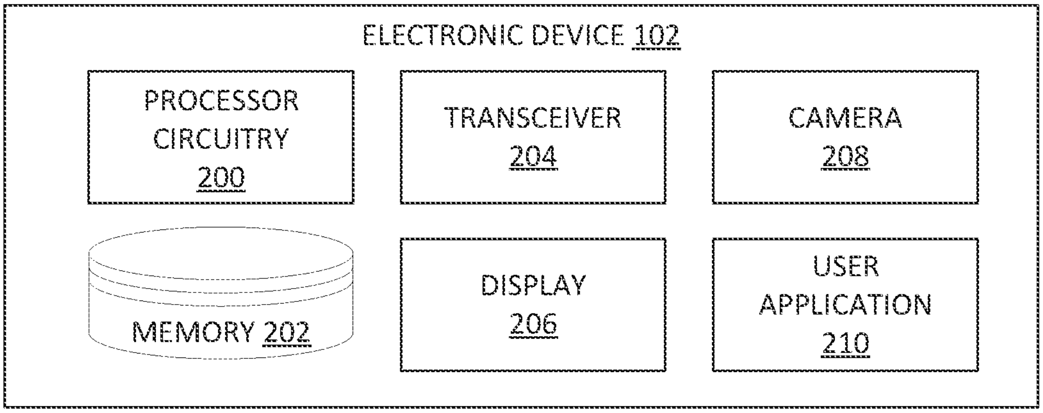
FIG. 2 is an example block diagram of the example user electronic device of FIG. 1.

FIG. 2 is a block diagram of the example electronic device 102. As disclosed above, in some examples, the electronic device 102 is implemented as a smartphone. However, in other examples, the electronic device 102 can be implemented as any other type of mobile or non-mobile electronic device. In this example, the electronic device 102 includes an example processor circuitry 200, an example memory 202, an example transceiver 204, an example display 206 (e.g., a capacitive touchscreen), and an example camera 208. The transceiver 204 can be any type of wired or wireless hardware, firmware, or software for enabling communication with other devices, such as via a wireless internet connection, Bluetooth®, Ethernet connection, etc. In the illustrated example, the electronic device 102 includes a user application 210, which can be used to communicate with the image analysis system 104 (FIG. 1). In some examples, the user application 210 is an application that is downloaded onto the electronic device 102. The user application 210 can be stored in the memory 202 and executed by the processor circuitry 200. While some of the example operations disclosed herein are described in connection with functions performed by the user application 210, these operations are not limited to functions performed by an application downloaded onto a device. Instead, the operations can be performed via a web browser or web-based applications. In some such examples, one or more of the operations can be performed remotely, such as by the image analysis system 104, and displayed on the electronic device 102. Also, in some examples, at least some of the operations of the user application 210 disclosed herein are cloud based, partially cloud based, or edge based.

Figure 3:
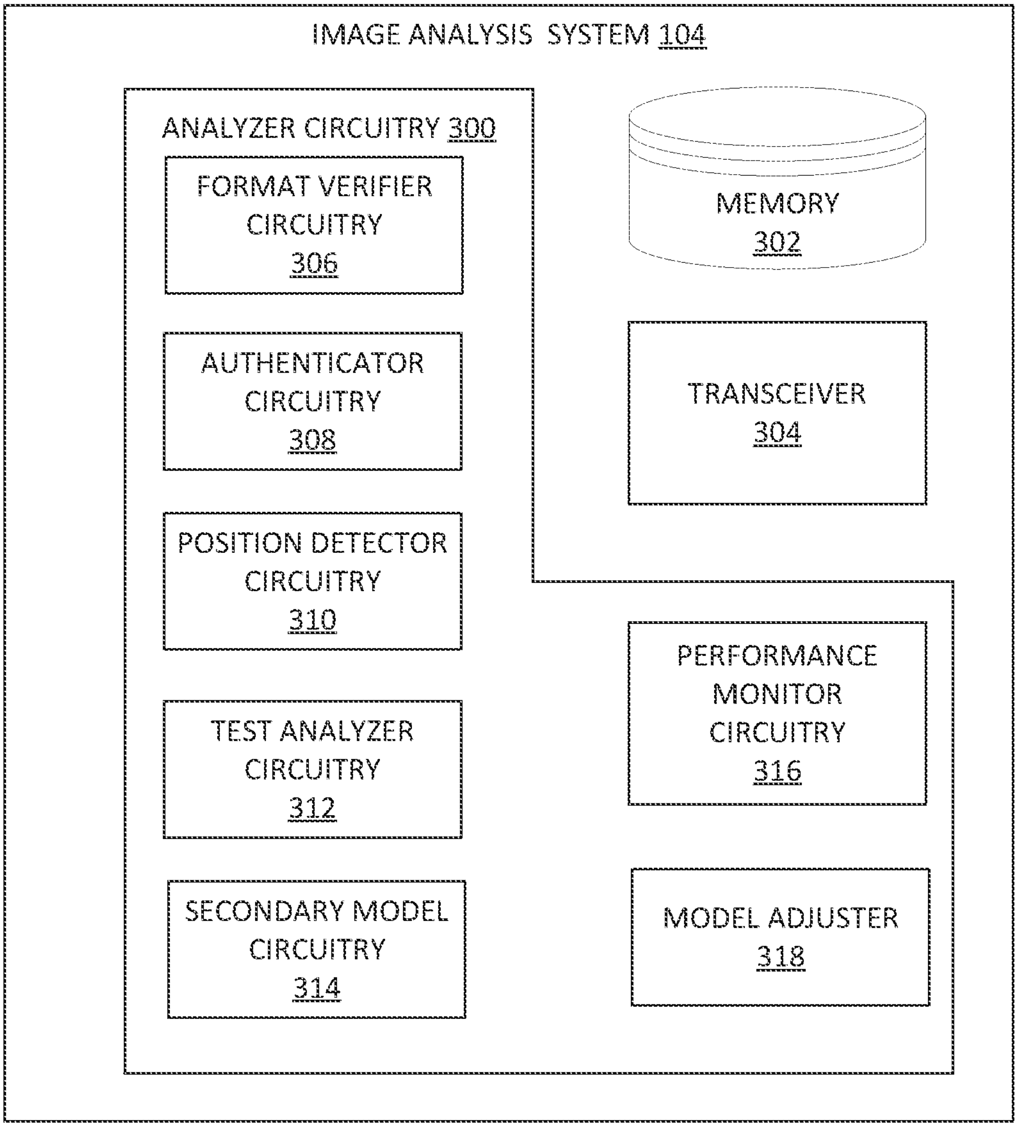
FIG. 3 is an example block diagram of the example image analysis system of FIG. 1.

FIG. 3 is a block diagram of the example image analysis system 104. The image analysis system 104 includes example analyzer circuitry 300, an example memory 302, and an example transceiver 304. The transceiver 304 communicates with the electronic device 102 (e.g., via the network 110). For example, the transceiver 304 can receive an image of the test strip 106 sent by the electronic device 102. The image can be stored in the memory 302. In some examples, the analyzer circuitry 300 removes metadata before storing the image, which reduces the amount of storage space needed. For example, the analyzer circuitry 300 can remove exchangeable image file format metadata prior to storing the image. In some examples, the memory 302 includes a database of user and/or user profiles. The image can be stored with the associated user/user profile. The analyzer circuitry 300 analyzes the image of the test strip 106 to determine the result of the test. The result can be stored in the memory 302 along with other identifying information (e.g., the date, the time, a test strip serial number, a type of test strip, etc.).

Figure 11:
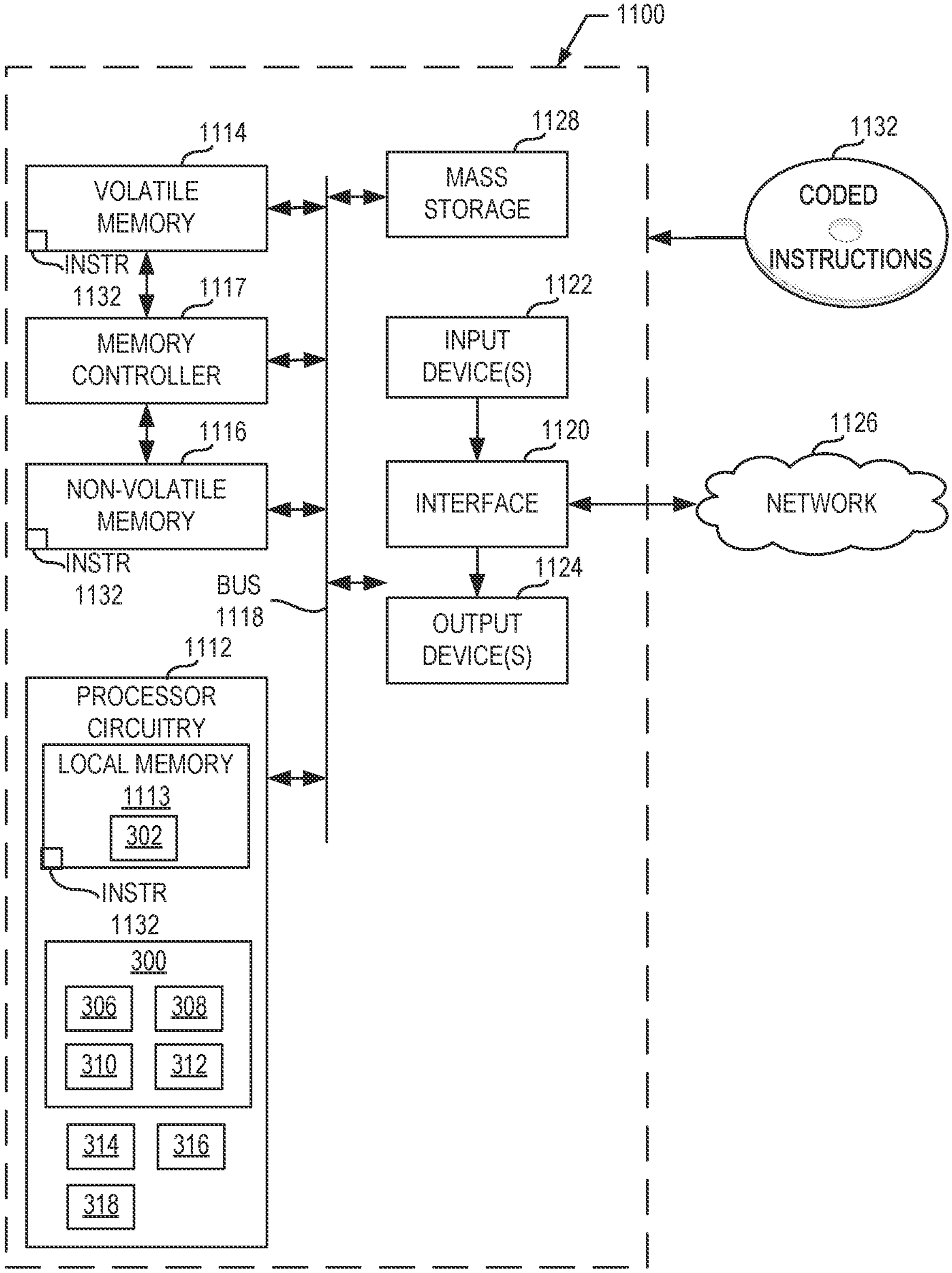
FIG. 11 is a block diagram of an example processing platform including processor circuitry structured to execute the example machine readable instructions of FIGS. 10A and 10B to implement the example analyzer circuitry of the example image analysis system of FIGS. 1 and 3.

The example analyzer circuitry 300 can be implemented by processor circuitry such as the processor circuitry 1112 disclosed in connection with FIG. 11. In the illustrated example, the analyzer circuitry 300 includes format verifier circuitry 306, authenticator circuitry 308, position detector circuitry 310, and result detection circuitry 312. The format verifier circuitry 306, the authenticator circuitry 308, the position detector circuitry 310, and the result detection circuitry 312 perform one or more operations to analyze an image of the test strip 106 and determine the result. In some examples, the analyzer circuitry 300 also includes secondary model circuitry 314 (which may also be referred to as second test analyzer circuitry), performance monitor circuitry 316, and model adjuster circuitry 318, which can be used to compare the result to a result from another model.

Figure 4:
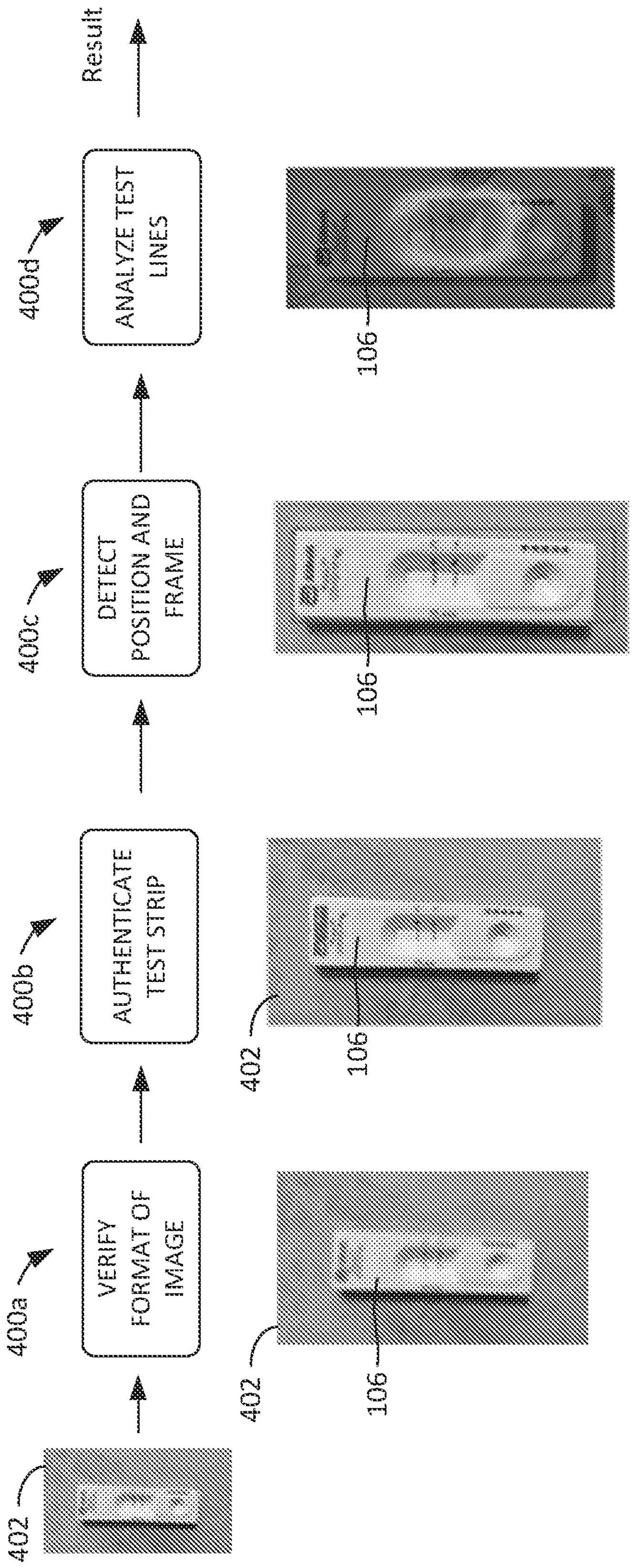
FIG. 4 illustrates an example process of analyzing an image of an LFA performed by the example image analysis system of FIGS. 1 and 3.

FIG. 4 illustrates an example process of operations or steps 400*a*-400*d* that may be performed by the analyzer circuitry 300 of the image analysis system 104 to analyze an image of the test strip 106. The image analysis system 104 receives an image 402 that was taken by the camera 208 of the electronic device 102 after the test was performed. In some examples, the user application 210 instructs the user on how to obtain an image with specific formatting to facilitate processing of the image by the user application 210 and/or the image analysis system 104. For example, the user application 210 may instruct the user to ensure the test strip 106 meets at least a minimum size and is large enough in the image, near a center of the image, meets minimum ambient light levels, and/or is within a certain degree of an orientation. For example, the user application 210 may instruct the user to position the test strip in the center of the image and within ±10° of a vertical position. In some examples, the user application 210 asks the user to verify the image is sufficient after capturing the image and before the image is sent. The user can judge whether the image appears to meet the one or more criteria identified herein before submitting. Additionally or alternatively, the user application 210 can perform one or more automated checks on the image to ensure the image satisfies the one or more criteria before sending. In some examples, if an error occurs in the image analysis process, the user application 210 can ask the user to retake and/or resubmit an image.

At step 400*a*, the format verifier circuitry 306 checks or verifies the image 402 meets the formatting standards or requirements for further analysis. In some examples, the format verifier circuitry 306 checks or verifies the format is sufficient by comparing one or more parameters or parameter values of the image 402 to one or more thresholds. For example, the format verifier circuitry 306 can verify the image 402 includes at least a threshold number of pixels (e.g., greater than 10,000 pixels). As another example, the format verifier circuitry 306 can verify the image 402 meets a threshold resolution level or aspect ratio, such as, for example, greater than 1920×1080 pixels. As another example, the format verifier circuitry 306 can verify the image 402 has at least a threshold brightness level (e.g., by comparing an average of the pixel brightness to a threshold). In some examples, the format verifier circuitry 306 determines if the image file format is one of an accepted file format such as, for example, a JPEG format, an Exif, a TIFF, a BMP format, a PNG format, etc. In some examples, the format verifier circuitry 306 only checks one parameter. In other examples, the format verifier circuitry 306 can check for multiple parameters.

In some examples, if the format verifier circuitry 306 determines that one of the parameters fails, the verifier circuitry 306 generates an error result for the image 402. The error result may be saved with the image 402 in the memory 302. In other examples, when the format verifier circuitry 306 determines that a parameter is not met, storage of the image is prevented. In such examples, insufficient images are not saved and computing resources are conserved. In some examples, the transceiver 304 transmits the error result to the electronic device 102, which is displayed to the user (an example of which is shown in further detail in connection with FIG. 5R). In some examples, if an error result is generated, the example process is stopped, thereby conserving computing power.

When the parameters are met (e.g., the parameter(s) satisfy the threshold(s)), the format verifier circuitry 306 determines the image 402 has a sufficient format and the process proceeds to step 400*b*. At step 400*b*, the authenticator circuitry 308 determines whether the test strip 106 in the image 400 is authentic. In some examples, the analyzer circuitry 300 is configured to interpret the results of a particular type or brand of test strip. Therefore, the authenticator circuitry 308 ensures the test strip 106 in the image 402 is the correct type or brand of test strip to be analyzed. Further, the authenticator circuitry 308 also verifies a test strip is present in the image 402. Therefore, if the image 402 does not contain a test strip, the image 402 can be disregarded and/or the authenticator circuitry 308 generates an error message to present to the user.

In some examples, to authenticate the test strip 106, the authenticator circuitry 308 executes a computer vision process on the image 402, such as Optical Character Recognition (OCR), to detect or identify target text on the test strip 106 (e.g., on the cartridge portion of the test strip 106), the cartridge) in the image 402. The target text may correspond to a brand, a manufacturer, a test type, a code, and/or other identifying information associated with the test strip 106. For example, in this example, the test strip 106 is a Panbio™ test strip manufactured by Abbott Laboratories, having headquarters in Abbott Park, IL, USA. In this example, the authenticator circuitry 308 searches for the text "Panbio" in the image 402, which corresponds to the brand of the test strip 106. As shown in step 400*b*, the authenticator circuitry 308 identified the text "Panbio" in the image 402. As such, the authenticator circuitry 308 determines the test strip 106 is authentic, and the process proceeds to step 400*c*. If the authenticator circuitry 308 does not identify or detect the target text in the image 402, the authenticator circuitry 308 generates an error result for the image 402. The error result may be saved with the image 402 in the memory 302. In other examples, the error result prevents storage of the image. In some examples, the transceiver 304 transmits the error result to the electronic device 102, which is displayed to the user (an example of which is shown in further detail in connection with FIG. 5R). In some examples, if an error result is generated, the example process is stopped, thereby conserving computing power.

In some examples, the authenticator circuitry 308 checks for the presence of one target text (e.g., "Panbio"). If the target text is not present, the authenticator circuitry 308 generates an error result. In other examples, the authenticator circuitry 308 may check for multiple target text. If one of the target text is identified, the image 402 passes the authentication step. In other examples, the authenticator circuitry 308 requires two target text to be present. For example, the authenticator circuitry 308 may check for the text "Panbio" (corresponding to the brand) and the text "Abbott" (corresponding to the manufacturer). If one of the target text is missing, the authenticator circuitry 308 generates an error result.

In some examples, the authenticator circuitry 308 implements and/or executes a machine learning model to determine whether the test strip is authentic. For example, the machine learning model can be used to detect the target text in the image 402. The machine learning model may be pre-trained. In some examples, the machine learning model is a CNN model (e.g., Generative Adversarial Network, LeNet, ResNet, EfficientNet, GoogleNet, VGG (e.g., VGGNET 16), DenseNet, and/or AlexNet). In other examples, other types of machine learning models can be implemented.

In some examples, after the target text is identified, the authenticator circuitry 308 highlights the text. For example, the authenticator circuitry 308 generates a boundary box (e.g., a rectilinear box) around the target text. In some examples, the boundary box is used in one or more other steps of the process.

In other examples, the authenticator circuitry 308 can authenticate the test strip 106 through other processes. For example, authenticator circuitry 308 can verify the authenticity by scanning and/or detecting a machine readable code, such as for example a barcode, Quick Response (QR) code, or Data Matrix code, that is on the test strip 106 in the image 402. If the authenticator circuitry 308 detects the correct machine readable code, the authenticator circuitry 308 interprets the machine readable code to obtain a serial number and compares the serial number to a list of authentic serial numbers. If the serial number matches one of the authentic serial numbers, the authenticator circuitry 308 verifies the authenticity and the process proceeds to step 400*c*. If the machine readable code is not present or does not contain the correct information (e.g., the serial number does not match one of the authentic serial numbers), the authenticator circuitry 308 generates an error result.

At step 400*c*, the position detector circuitry 310 detects the position and/or orientation of the test strip 106 to ensure the test strip 106 is in a sufficient position (e.g., in or near a target orientation) in the image 402 for further analysis. In some examples, it is advantageous to have the test strip 106 vertically aligned in the image 402, because the image height is generally greater than the image width. In some examples, the position detector circuitry 310 analyzes the image 402 to determine the angle of the test strip 106 in the image 402 relative to a vertical position. In some examples, the position detector circuitry 310 determines the position (e.g., angle relative to vertical) of the test strip 106 by determining the boundaries of the test strip 106 in the image and determining an axis (e.g., a vertical or longitudinal axis) of the test strip 106 based on the boundaries. Additionally or alternatively, the position detector circuitry 310 can determine the position of the test strip 106 based on the orientation of the boundary box of the target text identified in step 400*b*.

In some examples, the position detector circuitry 310 compares the angle of the test strip 106 in the image 402 to a threshold or threshold range. In some examples, the threshold is ±10° from a vertical position. In other examples, the threshold may be larger or smaller. If the position detector circuitry 310 determines the angle is meets or satisfies the threshold or threshold range (e.g., is within ±10° of the vertical position), the position detector circuitry 310 determines the test strip 106 is in a sufficient position, and the process proceeds to step 400*d*. In some examples, the image 402 is acceptable if the test strip 106 is upside down (rotated 180°) in the image 402. If the angle does not satisfy the threshold or threshold range (e.g., the test strip 106 is 90° from the vertical position (e.g., sideways or horizontal) in the image 400)), the position detector circuitry 310 generates an error result for the image 402. The error result may be saved with the image 402 in the memory 302. In other examples, the error result prevents storage of the image. In some examples, the transceiver 304 transmits the error result to the electronic device 102, which is displayed to the user (an example of which is shown in further detail in connection with FIG. 5R). In some examples, if an error result is generated, the example process is stopped, thereby conserving computing power.

In some examples, the analyzer circuitry 300 determines the desired or target orientation for the test strip 106 for image capture based on the type of test strip. For example, the physical dimensions of the test strip may be used to identify the target orientation. A vertical target orientation may be used for test strips that have a greater length than width to optimize pixel resolution.

In some examples, the position detector circuitry 310 determines that the target orientation is met, but an entire test strip (i.e., cartridge) is not captured in the image. In such examples, if the result detection circuitry 312 determines that test line(s) are visible in the image, the process may still continue.

At step 400*d*, the result detection circuitry 312 analyzes the image 402 to determine the result of the test. For example, the result detection circuitry 312 analyzes the image 402 to identify the test region 107, determine whether one or more lines are present in the test region 107, and determine the result of the test based on the presence and/or absence of the line(s). In some examples, the result detection circuitry 312 implements and/or executes a machine learning model to analyze the image to determine the result of the test. In some examples, the machine learning model classifies the image 402 as having a negative result, a positive result, or an invalid result. A negative or positive result may be generated based on the visual indicator(s) (e.g., the presence, absence, color, pattern, etc. of the test lines). In some examples, a particular color or degree or depth of a color is not analyzed but, rather, the negative or positive result is determined based on the presence or absence of a line regardless of color. An invalid result may occur if the line(s) are not readable or of an insufficient intensity. The result can be saved in the memory 302 associated with the image 402. The machine learning model may be pre-trained. In some examples, the machine learning model is a deep learning model, such as a CNN model (e.g., Generative Adversarial Network, LeNet, ResNet, EfficientNet, GoogleNet, VGG (e.g., VGGNET 16), DenseNet, and/or AlexNet). In other examples, other types of machine learning models can be implemented (e.g., a DNN model, an RNN, etc.). In some examples, the machine learning model implemented at step 400*d* is a different machine learning model that is implemented at step 400*b* (e.g., two different types of CNNs, a CNN and a DNN, etc.). In some examples, the result detection circuitry 312 performs a scaling method that uniformly scales all dimensions of depth/width/resolution using a compound coefficient. As disclosed above, in some examples, the analyzer circuitry 300 performs the operations 400*a*-400*d* in sequence, and only proceeds to the next operation in the sequence of operations 400*a*-400*d* if the previous/prior operation passes a check, verification, and/or satisfies a threshold. If one of the operations fails, the analyzer circuitry 300 stops or aborts the sequence of operations 400*a*-400*d*. This reduces or saves significant computing power and resources. For example, the analyzer circuitry 300 is to (a) determine whether a format of an image of a lateral flow assay device satisfies a format threshold (e.g., as disclosed in connection with operation 400*a*), (*b*) in response to determining the format of the image satisfies the format threshold, determine whether the lateral flow assay device in the image is authentic (e.g., as disclosed in connection with operation 400*b*), (*c*) in response to determining the lateral flow assay device is authentic, determine whether a position of the lateral flow assay device in the image satisfies a position threshold (e.g., as disclosed in connection with operation 400*c*), and (*d*) in response to determining the position of the lateral flow assay device satisfies the position threshold, analyze the image to determine the result of the diagnostic test (e.g., as disclosed in connection with operation 400*d*). Further, the analyzer circuitry 300 is to (e) abort the sequence of the operations 400*a*-400*d* during performance of the sequence of operations 400*a*-400*d* at the time any one of operations 400*a*-400*c* fails. In some examples, the analyzer circuitry 300 generates an error message upon failure of any one of the operations 400*a*-400*d* and transmits the error message to the electronic device 102.

In some examples, the image analysis system 104 transmits the result to the disease tracker(s) 108. Additionally or alternatively, in some examples, the image analysis system 104 transmits the result to the electronic device 102 (examples of which are shown in further detail in connection with FIGS. 5O, 5P, and 5Q). However, in other examples, the image analysis system 104 may not transmit the result to the electronic device 102.

In some examples, the image analysis system 104 may operate at a central server remote from the electronic device 102. In some examples, the image analysis system 104 is cloud-based. In some examples, the image analysis system 104 operates in edge-based architecture. For example, the image analysis system 104 operates on one or more edge servers such as, for example, edge appliances that may be hosted by a medical facility, a telecommunication company, a government, or other entity. Edge-based operation reduce latency to provide results and other processing more quickly.

Figure 5B:
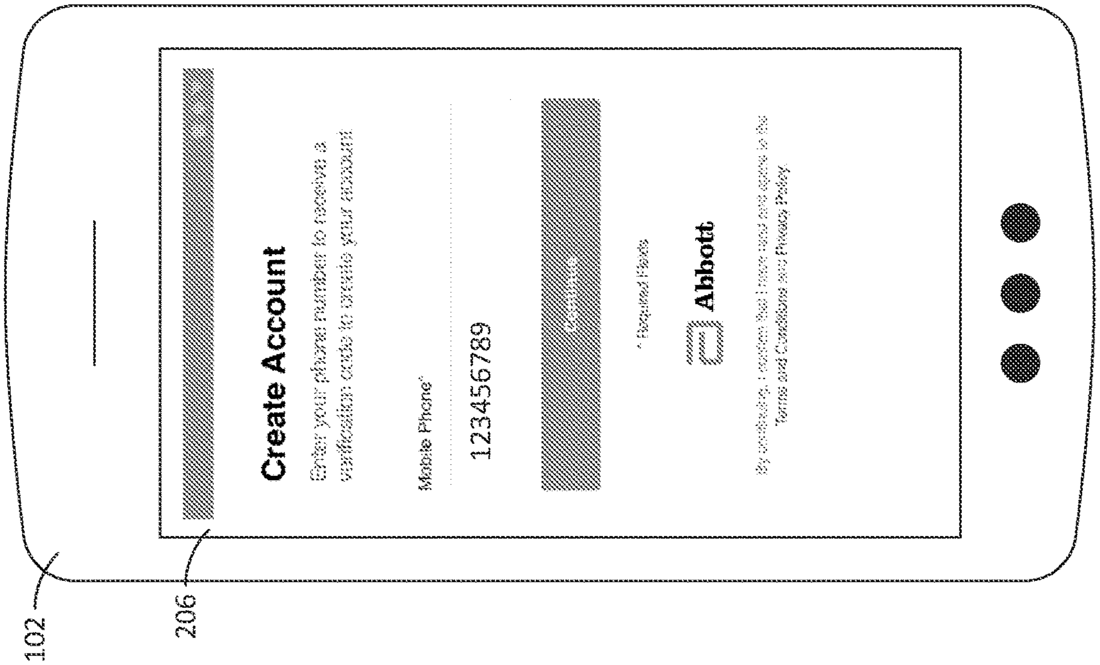
FIGS. 5A-5S are example user interface screens that can be presented on the example electronic device of FIG. 1.
Figure 5A:
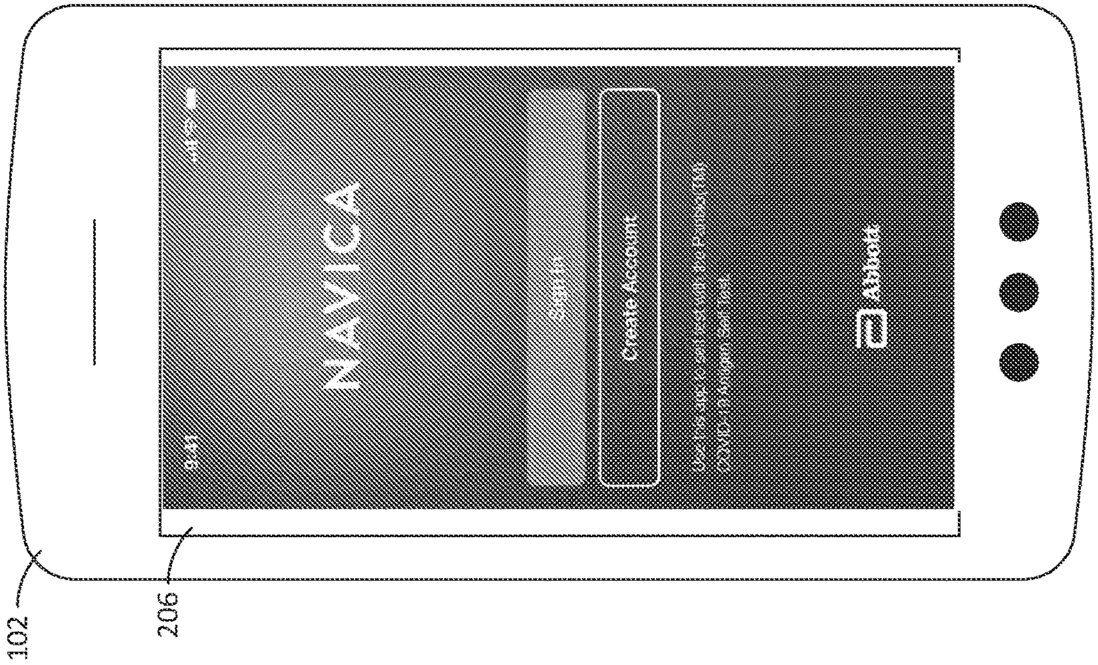
Figure 5D:
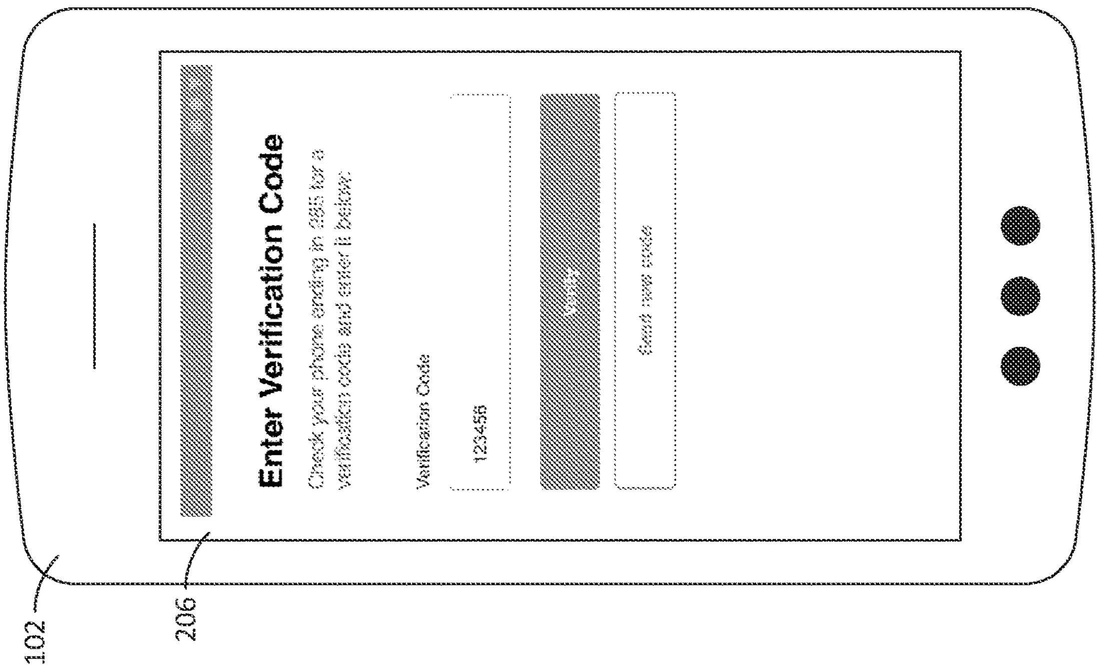
Figure 5C:
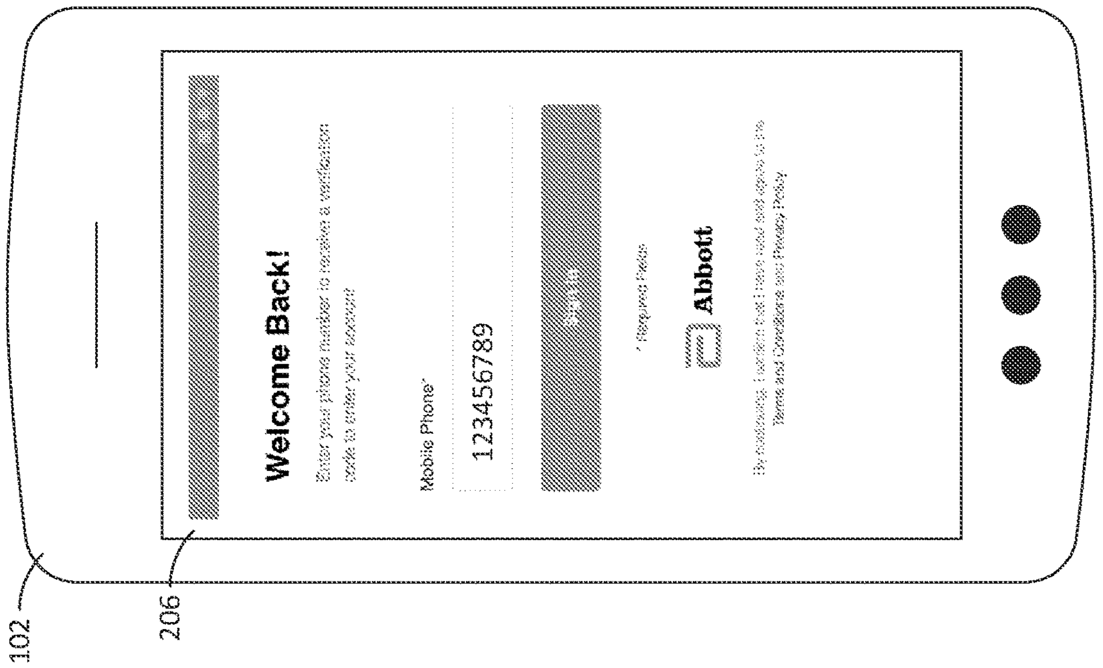
Figure 5E:
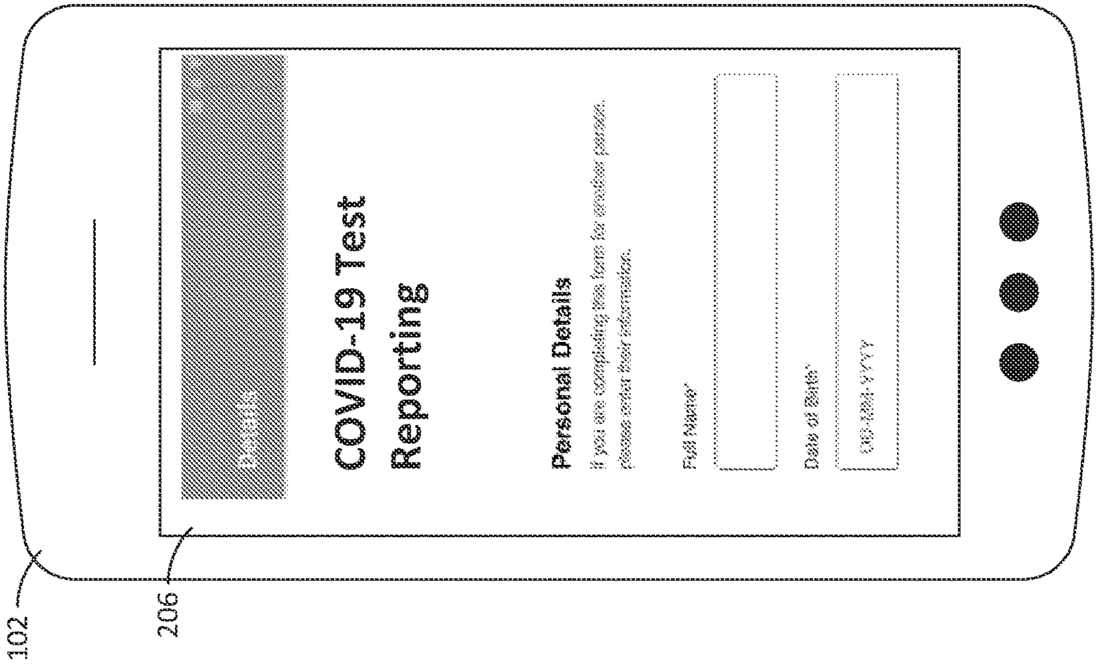
Figure 5F:
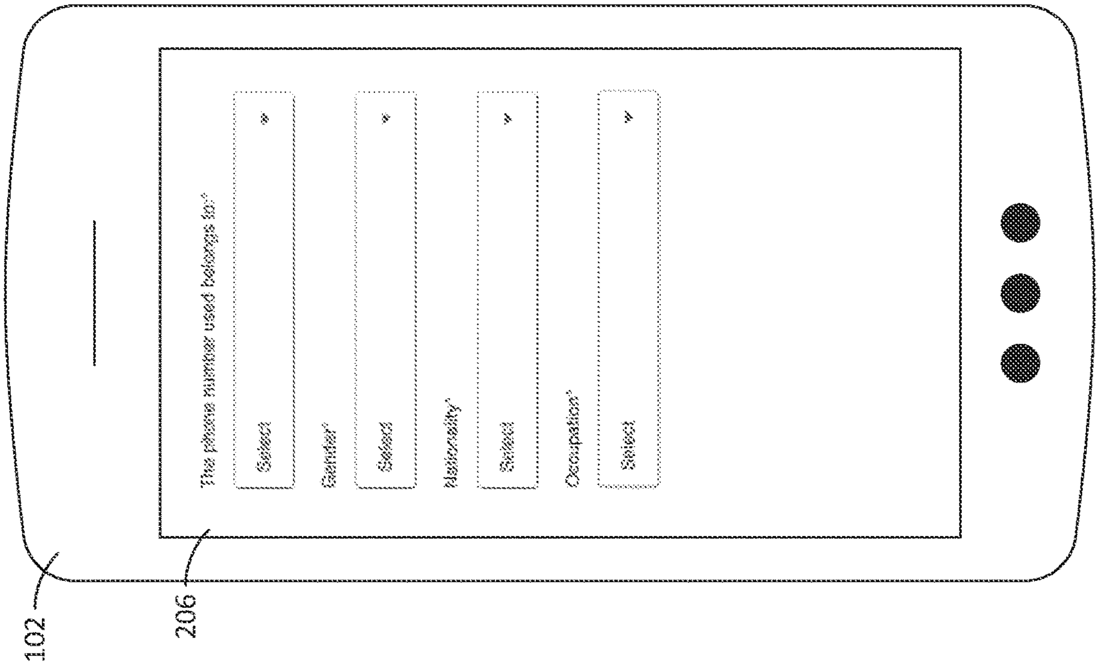
Figure 5H:
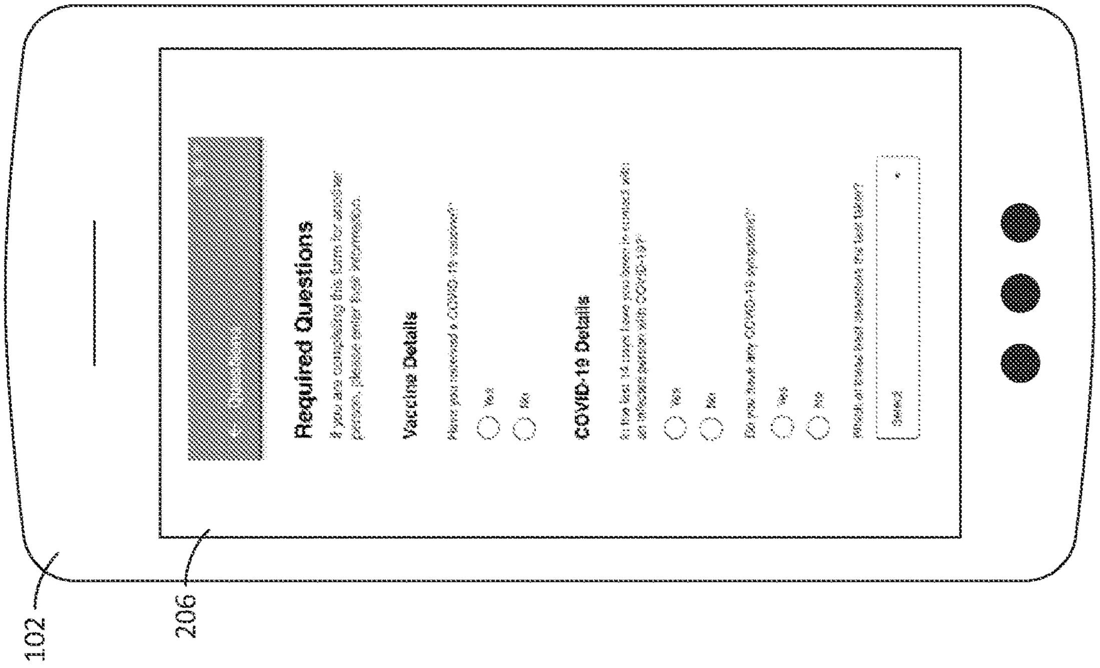
Figure 5G:
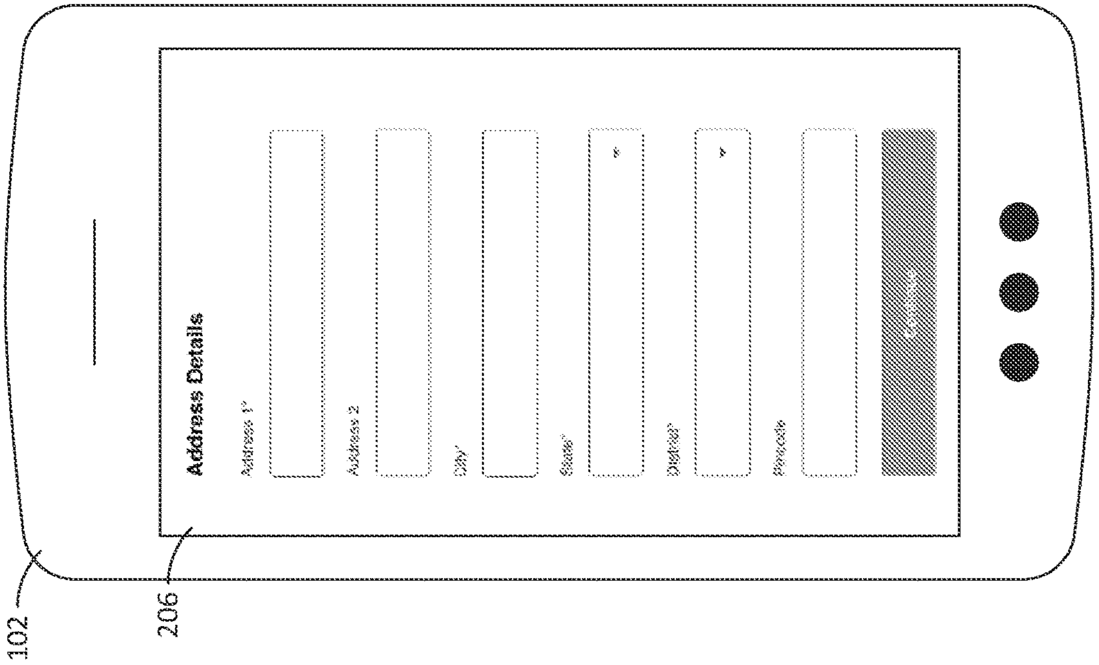
Figure 5J:
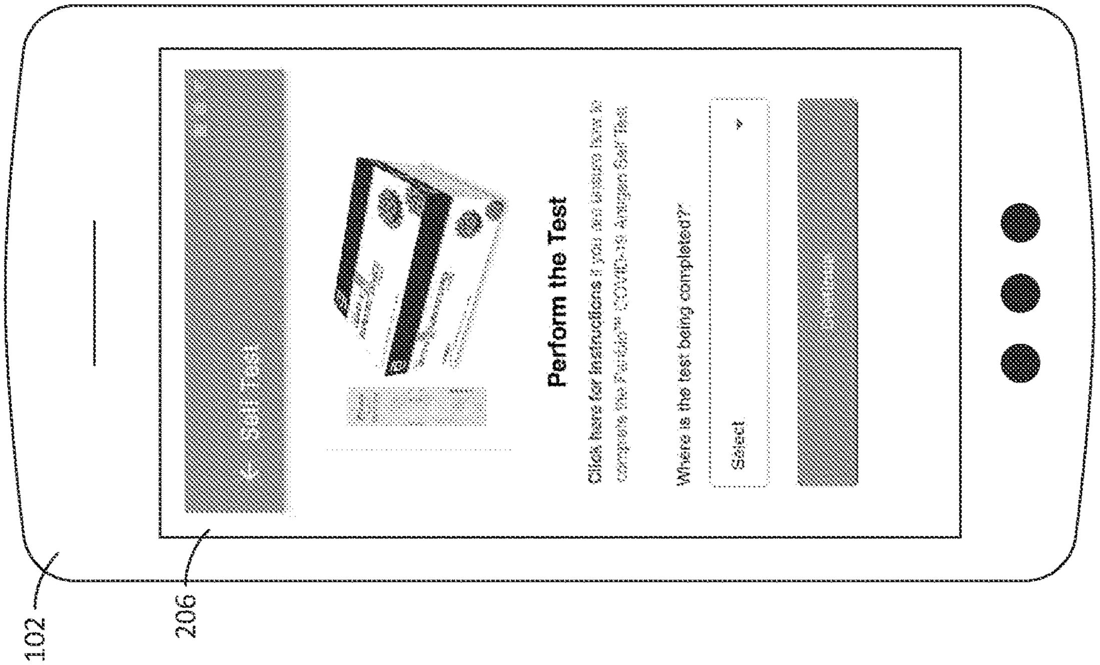
Figure 5I:
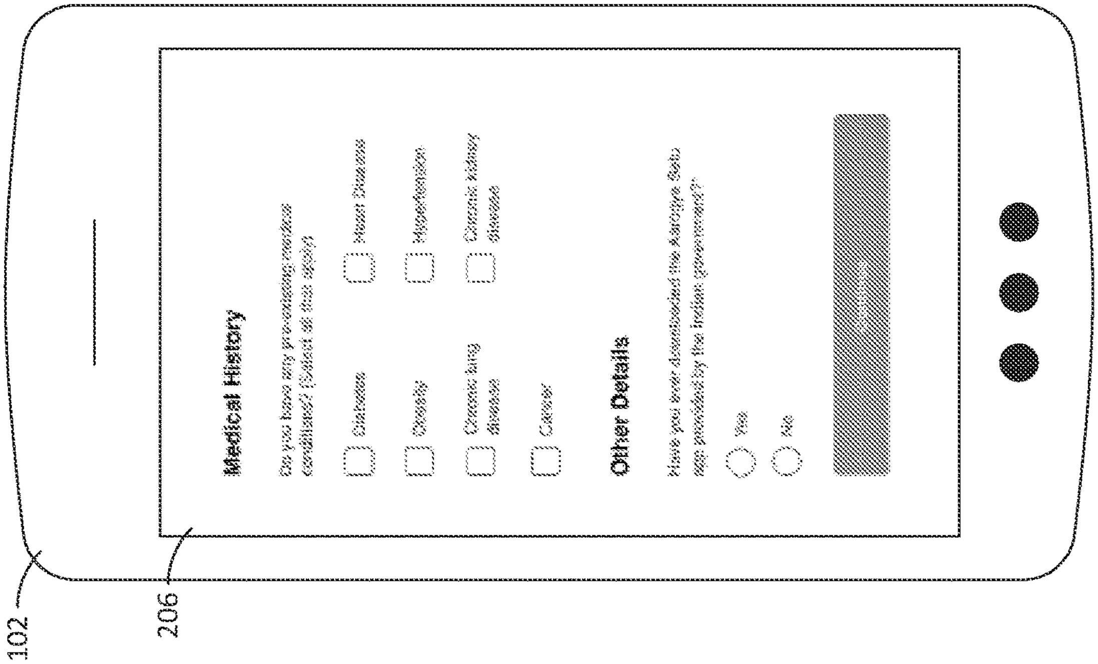
Figure 5L:
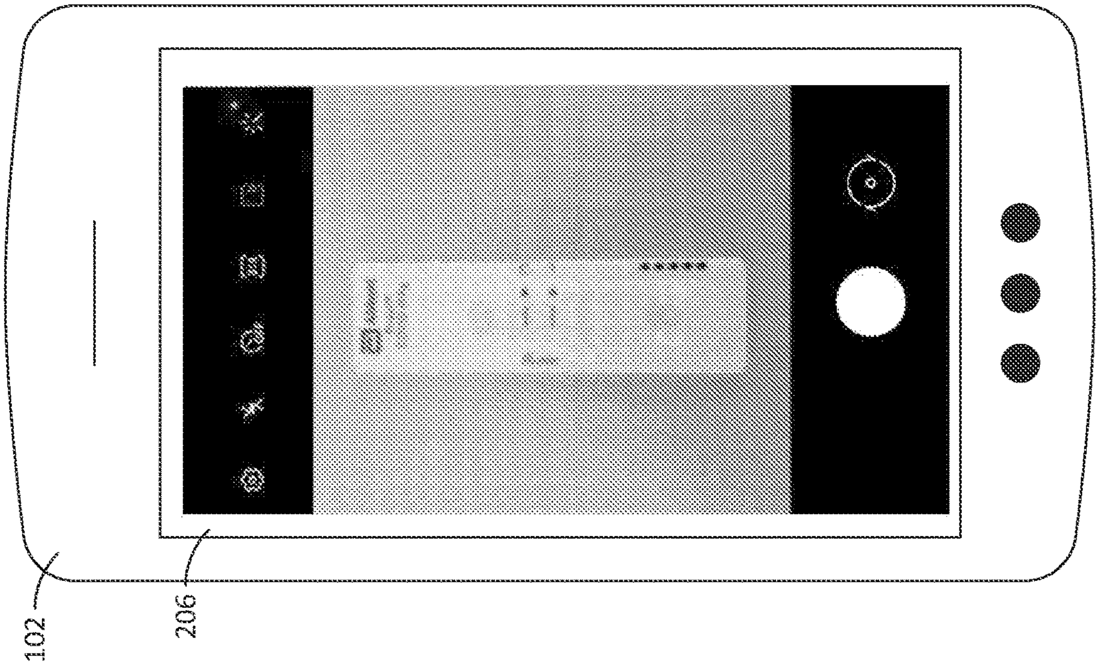
Figure 5K:
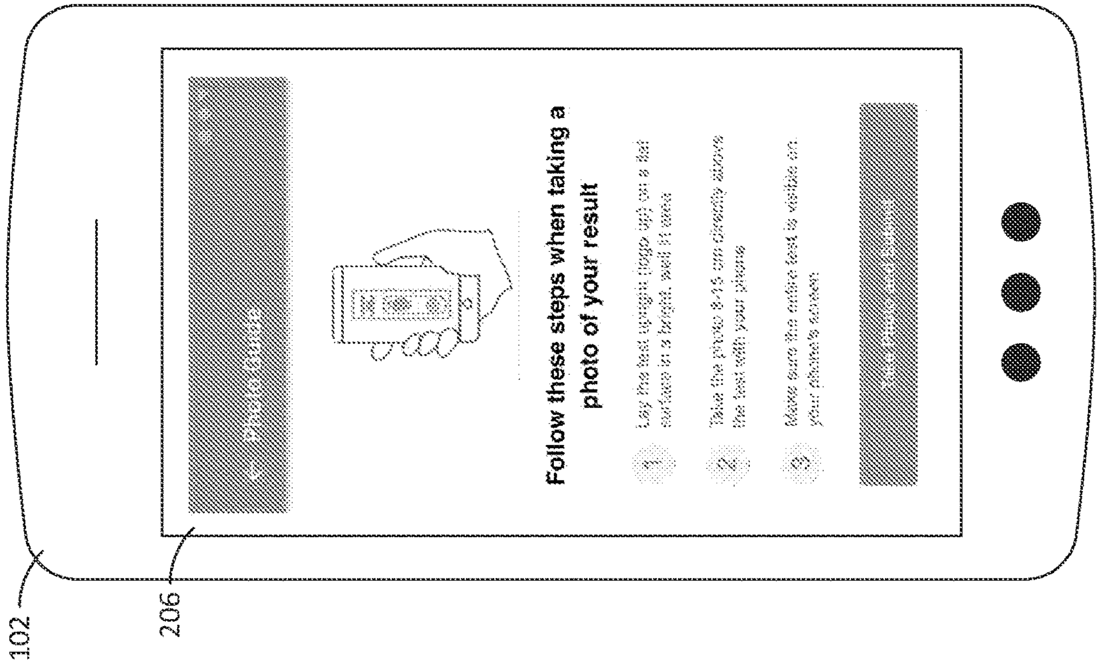
Figure 5M:
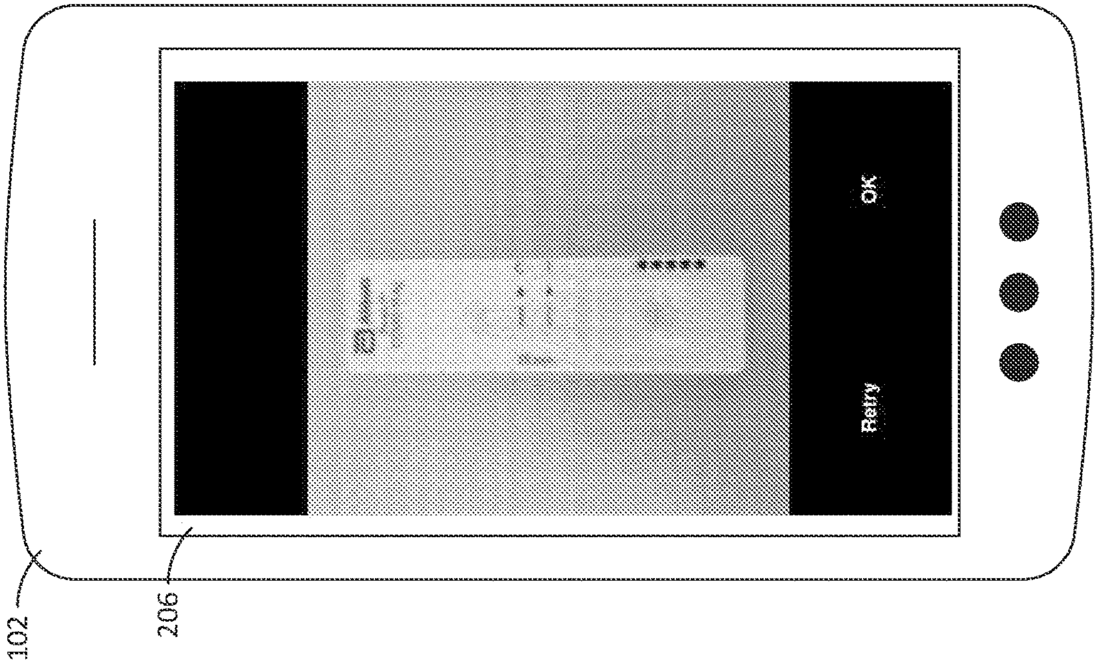
Figure 5N:
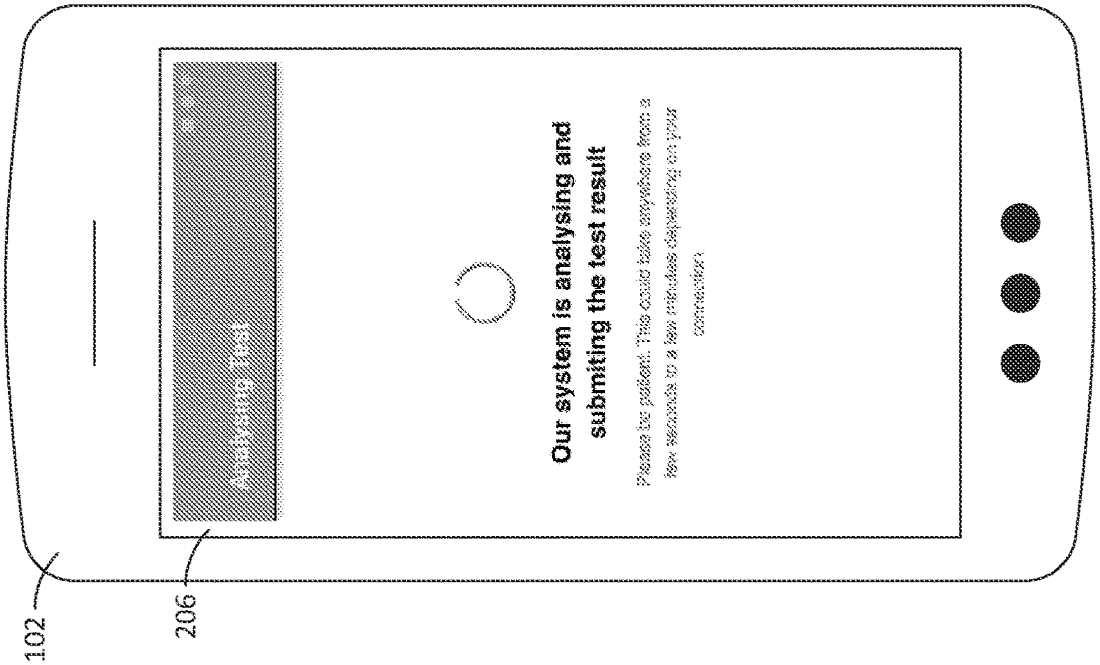
Figure 5O:
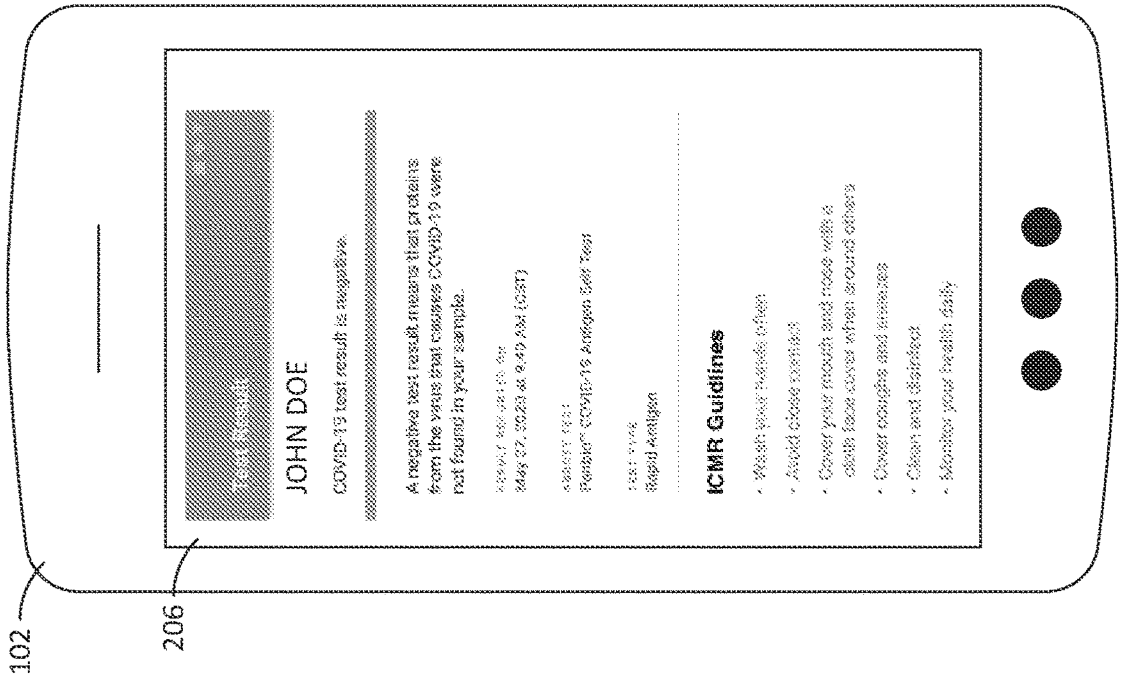
Figure 5P:
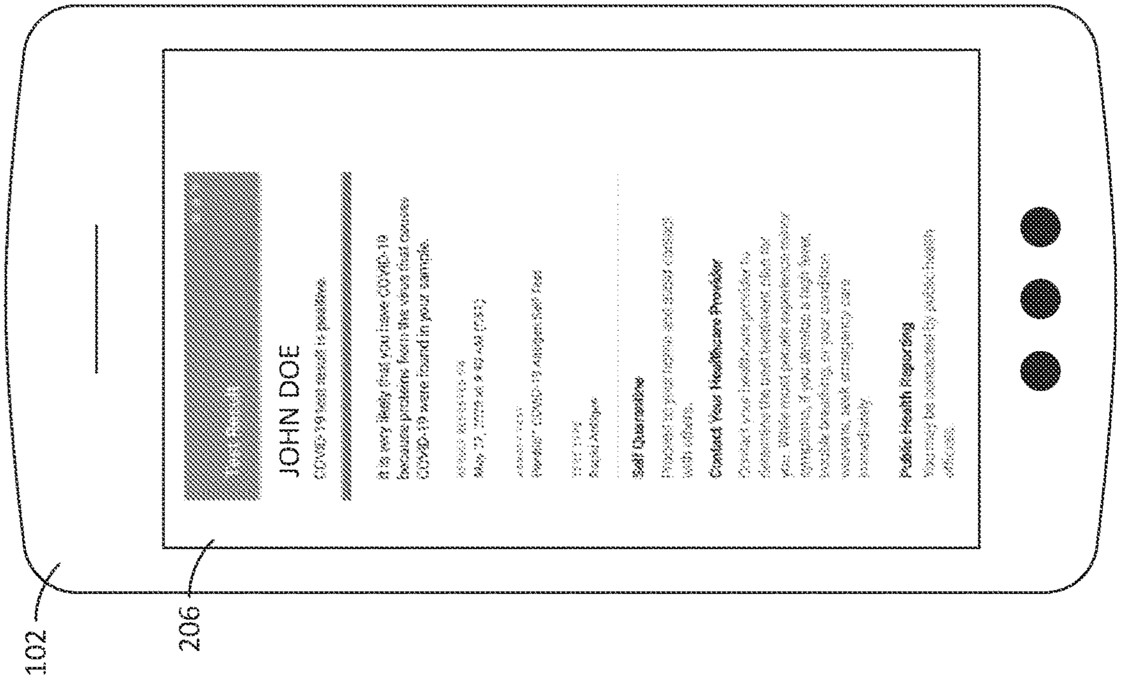
Figure 5Q:
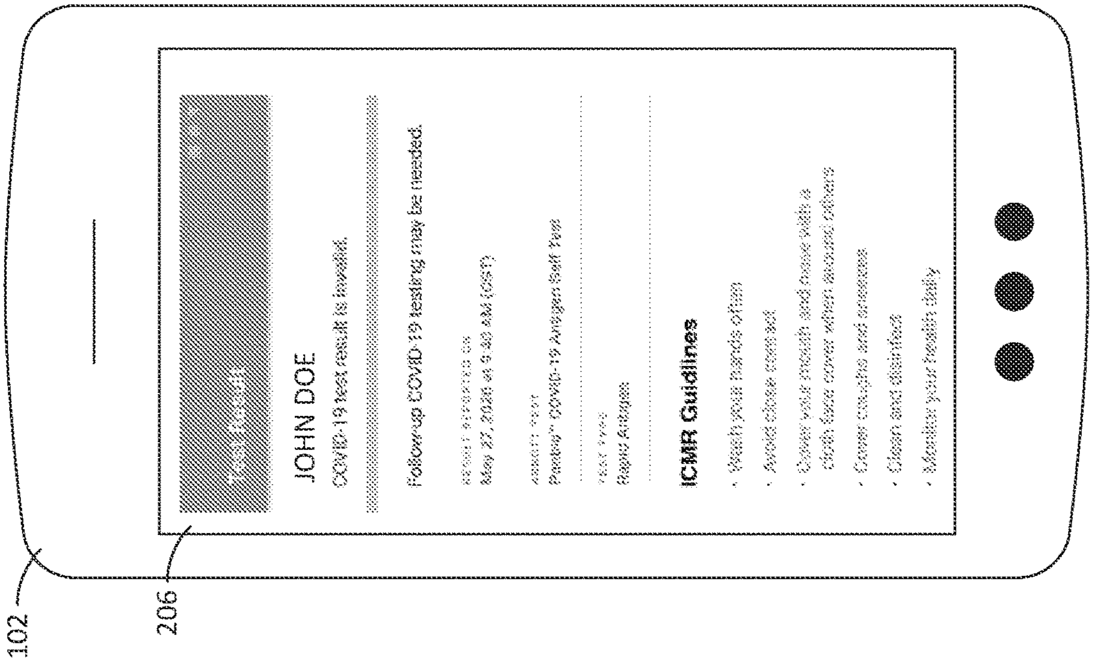
Figure 5R:
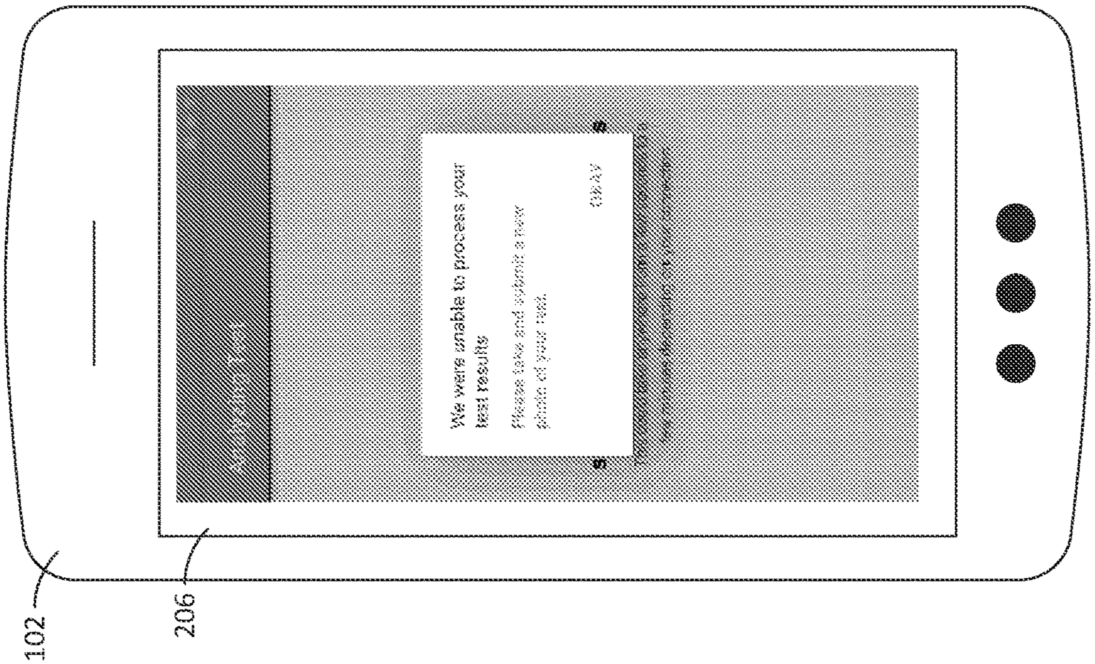
Figure 5S:
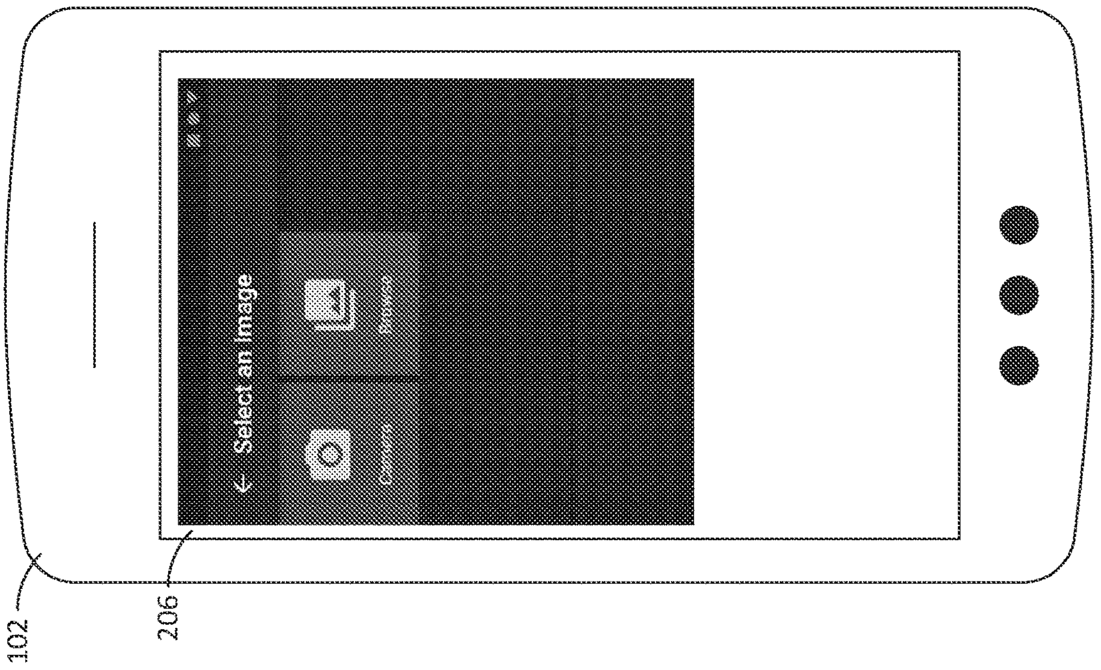

FIGS. 5A-5S are example user interface screens that can be presented on the display 206 of the example electronic device 102 during a process for obtaining an image of a test strip and submitting the image to the image analysis system 104. The example user interface screens may be presented by the user application 210 on the display 206. The example process is described in connection with the user being tested for COVID-19. However, it is understood that the example process could be similarly performed in connection with assays for detection for any analyte of interest including analytes associated with the presence of an infectious disease and/or for multiple tests or assays for multiple analytes of interest or diseases. Further, while the example process in described in connection with one test strip 106, the example process can be similarly implemented in connection with multiple test strips from one user (e.g., multiple test strips in the same image and/or in more than one image) and/or one test strip that detects multiple target analytes. Therefore, multiple tests can be analyzed at the same time.

As disclosed above, the user can download the user application 210 on the electronic device 102. FIG. 5A shows an initial screen presented on the display 206 when the user opens the user application 210 on the electronic device 102. If the user does not have an account, the user can create a new account (by selecting the "Create Account" button). FIG. 5B shows an interface screen for the user to enter a phone number to create a new account. If the user has an account already established, the user can sign in (by selecting the "Sign In" button). FIG. 5C shows an interface screen for the user to enter their phone number. The user application 210 transmits the phone number to the image analysis system 104. For security purposes, in some examples, the image analysis system 104 transmits a verification code to the electronic device 102 (e.g., via text message, via email, etc.). As shown in FIG. 5D, the user can enter the verification code. The user application 210 transmits the verification code to the image analysis system 104. In other examples, the process may not use a verification code. Additionally or alternatively, the user can log in with a user name and password and/or a biometric scan, for example.

As shown in FIGS. 5E, 5F, and 5G, the user can enter identifying information, such as their full name, date of birth, address, etc. The user application 210 transmits the information to the image analysis system 104. The information may be stored in a user account profile in the memory 302.

As shown in FIGS. 5H and 51, the user application 210 provides a medical questionnaire that asks the user about their status relative to COVID-19 (e.g., whether they are vaccinated, have any symptoms, etc.) and other medical questions. The information is sent to the image analysis system 104 and stored with the user's account profile. In FIG. 5J, the user selects where the test is being performed.

Figure 9:
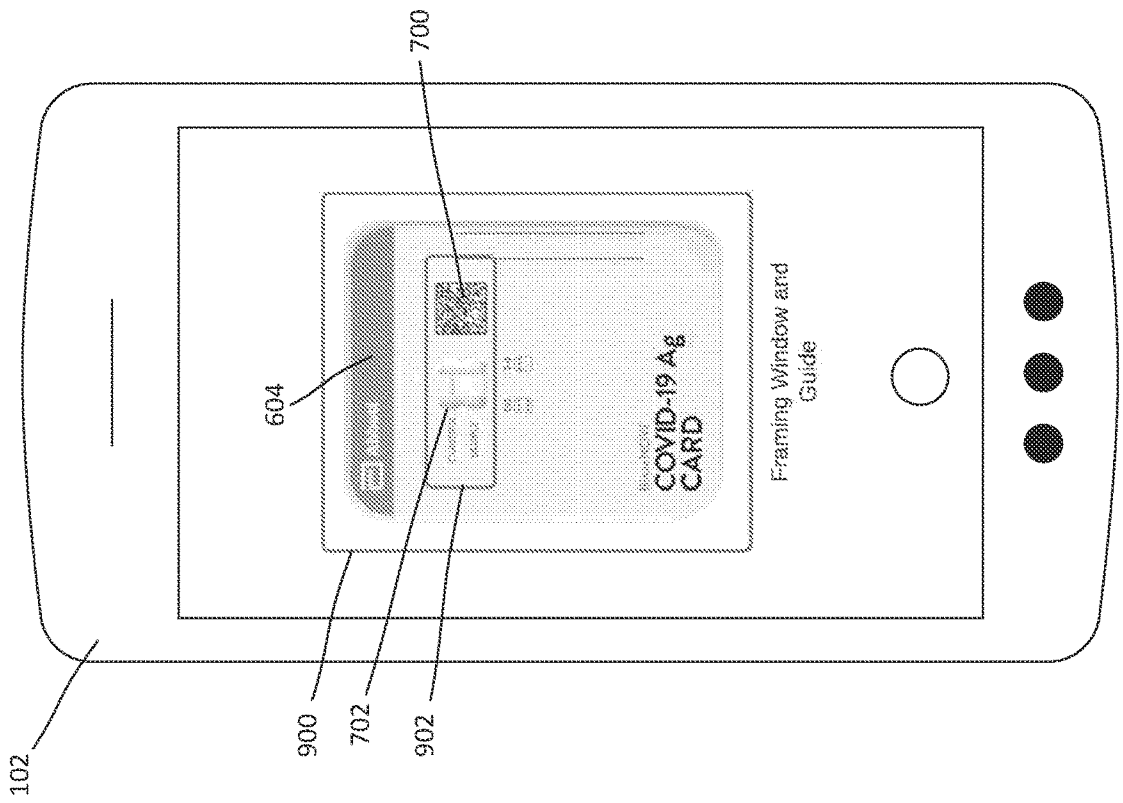
FIG. 9 shows an example user interface screen with frames for capturing an image of the example LFA of FIGS. 7 and 8.

In FIG. 5K, the user application 210 displays a list of guidelines or suggestion on how to take a sufficient image of the test strip 106. This helps ensure the image is sufficient or acceptable for analysis purposes by the image analysis system 104. Example guidelines or suggestions include ensuring the test strip 106 is large enough in the image, the test strip 106 is in the center of the image, there is good ambient light, and/or the test strip 106 is oriented in a particular position such as, for example, vertically (e.g., within 10° of vertical) in the image. The user can select the button to take a photo. The user application 210 accesses the camera 208 and displays the feed from the camera 208 as shown in FIG. 5L. In some examples, the interface screen augments the image with alignment markers. For example, the interface screen may present a rectangular alignment box overlaid on the camera feed (an example of which is shown in FIG. 9). This helps guide the user to properly align or position the test strip 106 in view of the camera 208. In other examples, an alignment box or other marker may not be presented. When the user is satisfied with the position, the user can select to take the picture (e.g., by pressing the camera shutter button on the interface).

In FIG. 5M, the user application 210 shows the image 402 that was captured and asks the user whether to accept the image 402 or take another image. If the user accepts the image, the user application 210 transmits the image 402 to the image analysis system 104. FIG. 5N shows a loading screen while the image 402 is being analyzed by the image analysis system 104.

As disclosed above, in some examples, the image analysis system 104 transmits the result to the electronic device 102. In some examples, the result can be either negative, positive, invalid, or error. FIG. 5O shows an example interface if the result is negative, FIG. 5P shows an example interface if the result is positive, FIG. 5Q shows an example interface if the result is invalid, and FIG. 5R shows an example interface if there is an error. If there is an invalid or error result, the user may take another image and re-submit it. In some examples, the user can take a new image or submit a saved image. FIG. 5S shows an option to allow the user to access the camera 208 for taking a new image or the user's photo library for submitting a previously taken image. In some examples, the error message may be presented during the image capture process and before an image is sent to the image analysis system 104.

Figure 6:
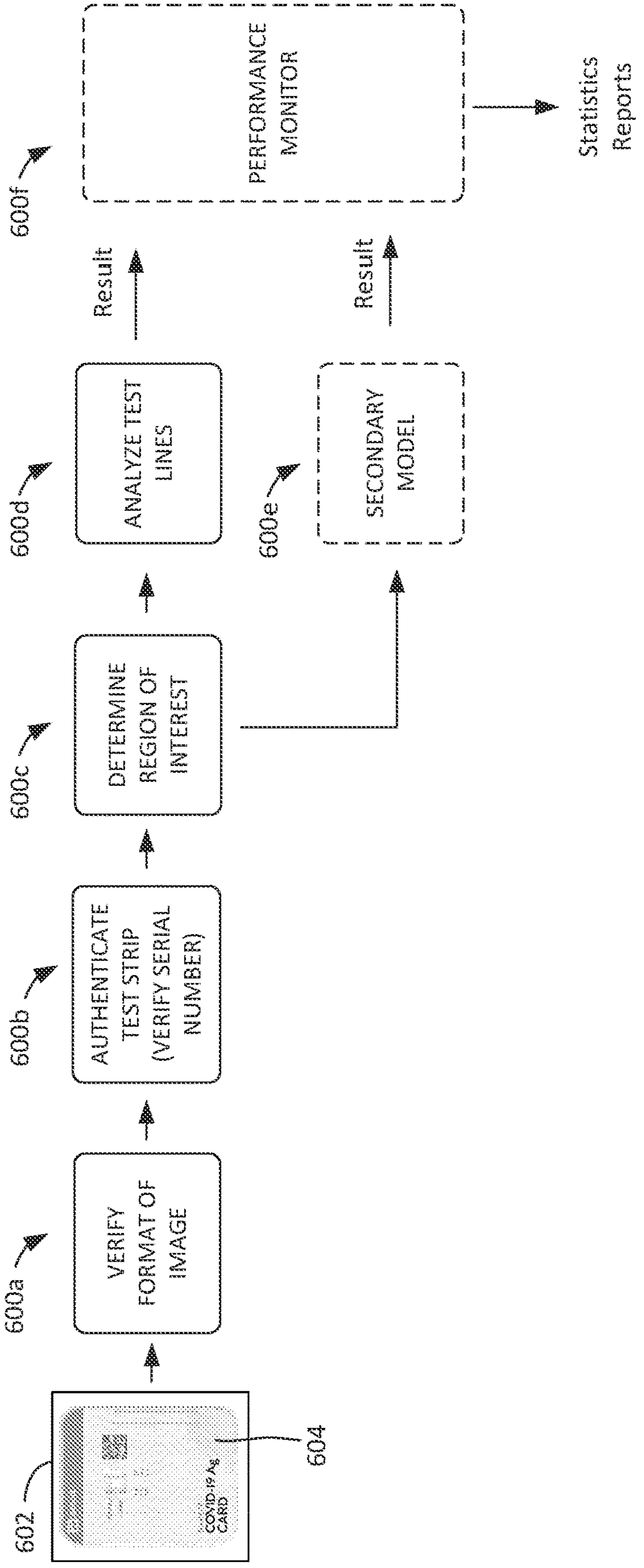
FIG. 6 illustrates another example process of analyzing an image of an LFA performed by the example image analysis system of FIGS. 1 and 3.

FIG. 6 illustrates another example process of operations or steps 600*a*-600*f* that may be performed by the image analysis system 104 to analyze an image of a test strip. Some of example operations or steps 600*a*-600*f* are the same or substantially the same as the example operations or steps 400*a*-400*d* disclosed above. Thus, some of the example operations or steps will not be repeated herein. The example operations or steps 600*a*-600*f* are described in connection with an image 602 of another type of test strip 604. In particular, in this example, the test strip 604 is a BinaxNOW™ test strip manufactured by Abbott Laboratories, having headquarters in Abbott Park, IL, USA. However, in other examples, the test strip 604 can be any type of test strip.

At step 600*a*, the format verifier circuitry 306 checks or verifies that the image 602 meets the formatting standards or requirements (e.g., format, size, resolution, clarity, etc.) for further analysis, which is the same as disclosed in connection with step 400*a* of FIG. 4. If the format verifier circuitry 306 determines that one or more of the parameter(s) fail(s), the verifier circuitry 306 generates an error result for the image 602. If the parameter(s) is/are met, the format verifier circuitry 306 determines the image 602 has a sufficient format and the process proceeds to step 600*b*.

Figure 7:
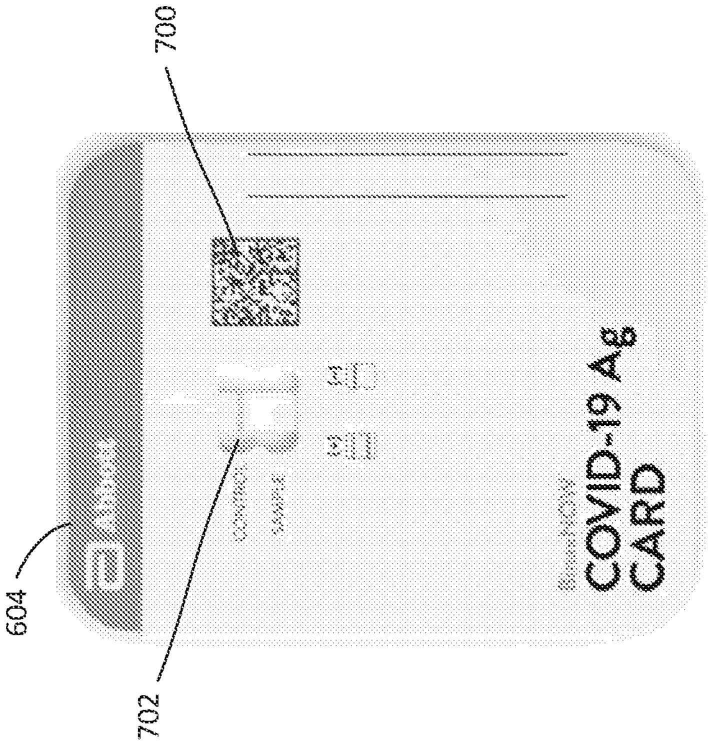

At step 600*b*, the authenticator circuitry 308 authenticates the test strip 604 in the image 602. As disclosed above, in some examples, the authenticator circuitry 308 can verify the authenticity of the test strip 604 by scanning a machine readable code on the test strip 604. For example, FIG. 7 is an enlarged view of the test strip 604. As shown in FIG. 7, a machine readable code 700 is printed and/or otherwise displayed on the test strip 604. In this example, the machine readable code 700 is a Data Matrix code. The authenticator circuitry 308 detects and interprets the machine readable code 700. In some examples, the authenticator circuitry 308 implements code scanning software or application, such as Cognex Software Development Kit (SDK), to detect and interpret the machine readable code 700. In some examples, the machine readable code 700 contains a serial number, which may be a unique serial number assigned to the test strip 604 and/or a lot or batch of test strips. The authenticator circuitry 308 interprets the machine readable code 700 to obtain the serial number. The authenticator circuitry 308 may compare the serial number to a list of serial numbers (e.g., provided by the manufacturer) to ensure the serial number is valid and/or the test strip 604 has not been previously used. If the authenticator circuitry 308 determines the serial number is not valid (e.g., does not match a serial number from the list, is associated with a test kit already used, etc.), the authenticator circuitry 308 generates an error result. Otherwise, if the authenticator circuitry 308 determines the serial number is valid, the authenticator circuitry 308 verifies the authenticity and the process proceeds to step 600*c*.

Figure 8:
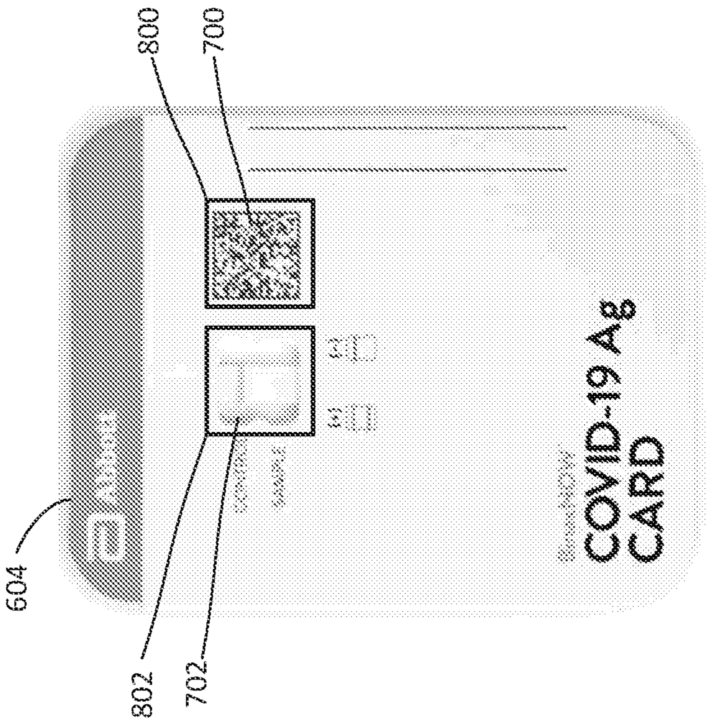
FIGS. 7 and 8 show an example LFA that may be analyzed in connection with the example process of FIG. 6.

At step 600*c*, the position detector circuitry 310 determines or identifies the region of interest in the image 402. In particular, the position detector circuitry 310 identifies a sub-region of the image 602 containing a test region 702 (FIG. 7) on the test strip 604. In this example, the position determiner circuitry 310 determines the location of the test region 702 based on the location of the machine readable code 700. For example, the authenticator circuitry 308 that detects the machine readable code 700 can also determine the location (e.g., coordinates), orientation, and size of the machine readable code 700 in the image 602. For example, as shown in FIG. 8, a boundary box 800 is shown around the machine readable code 700, which may be determined by the authenticator circuitry 308 and/or the position detector circuitry 310. Based on the location, orientation, and size of the machine readable code 700 and/or the boundary box 800, the position detector circuitry 310 determines or identifies the location and scale of a sub-region 802 of the image 602 containing the test region 702. For example, the test region 702 may be a known distance and size/scale relative to the machine readable code 700. The position detector circuitry 310 can perform adaptive cropping and/or resizing.

In some examples, one or more frames, windows, or guides can be used to help identify the machine readable code 700 and/or the test region 702 in the image 602. For example, FIG. 9 shows the test strip 604 as displayed on the electronic device 102 from the camera feed. The user application 210 displays a first guide 900 and a second guide 902. The user is to move the electronic device 102 and/or the test strip 604 to align the test strip 604 within the first guide 900 and the machine readable code 700 and/or the test region 702 within the second guide 902. When the user has aligned the position of the first guide 900 and the second guide 902, the user can select capture an image to take the picture (e.g., by pressing the camera shutter button on the interface). In some examples, the framed sections are used to identify the machine readable code 700 and the sub-region 802 (FIG. 8) containing test region 702 at steps 600*b* and 600*c*. Therefore, in some examples, using the guides 900, 902 reduces errors when analyzing the image. In some examples, only the portion of the image within the second guide 902 is transmitted to the image analysis system 104. Also, in the illustrated example, the first guide 900 and the second guide 902 are shown as rectangles. In other examples, other markings may be used for the guides 900, 902 including, for example, cross-hairs, dots, arrows, etc.

At step 600*d*, the result detection circuitry 312 analyzes the image 602 and, more particularly, the sub-region 802 containing the test region 702, to determine the result of the test. This step can be conducted in a similar manner as step 400*d* disclosed above. In some examples, the result detection circuitry 312 returns a result of positive, negative, or invalid. In some examples, the result detection circuitry 312 utilizes a machine learning model (e.g., a CNN model such as EfficientNet) to analyze determine the result.

Additionally or alternatively, in some examples, another model independently analyzes the image 602 to determine or calculate the result. For example, at step 600*e*, the secondary model circuitry 314 independently analyzes the test region 702 to determine the result of the test. In some examples, the secondary model circuitry 314 analyzes the test region 702 using a line detector model or a machine learning model. The machine learning model implemented by the secondary model circuitry 314 can be different (e.g., a different type and/or training with different training data) than the machine learning model implemented by the test analyzer circuitry 312. In some examples, the result detection circuitry 312 analyzes the image 602 using a first machine learning model and the secondary model circuitry 314 analyzes the image 602 using a second machine learning model in parallel. The secondary model circuitry 314 may also output a result of positive, negative, or invalid, similar to the image analysis conducted in step 600*d*. The results from steps 600*d* and 600*e* are sent to the performance monitor circuitry 316. At step 600*f*, the performance monitor circuitry 316 compares the results from steps 600*d* and 600*e* and generates statistics regarding the results, such as, for example, the number of times the results are the same, different, etc. In some examples the statistics are output as a report. In some examples, these statistics can be used to adjust or modify the machine learning model implemented at step 600*d*. For example, if the results are routinely different, the programmers can adjust one or more parameters of the machine learning model executed by the test analyzer circuitry 312. In other examples, the model adjuster 318 can automatically adjust one or more of its parameters of the machine learning model based on the statistics (e.g., the comparison(s)) or the differences in the results.

In some examples, the performance monitor circuitry 316 identifies images for manual review if there are differences in the results. For example, if the results do not match, the performance monitor circuitry 316 can flag the image 602 to be reviewed by a person. The person can then manually review the image and determine and input the result.

An example timeline or sequence of events as experienced by the user using the user application 210 is disclosed below. The example operations may be implemented in addition to or as an alternative to the user interface screens shown in FIGS. 5A-5S. In some examples, before performing the test, the user uses the electronic device 102 to scan a code on a box containing the test strip 604 and/or a code (e.g., the machine readable code 700) on the test strip 604. The codes may be barcodes, QR codes, Data Matrix codes, etc. The code on the box and/or the code on the test strip 604 may contain unique or quasi-unique serial numbers. In some examples, the user application 210 saves the serial number(s) with the user's account profile in the memory 202 and/or transmits the serial number(s) to another system (e.g., an application data server) to be stored with the user's profile. In some examples, the user application 210 may transmit the serial number(s) to the image analysis system 104 or another system to verify the validity of the test strip. In some examples, the serial number(s) are saved with the user's account profile prior to submission to the image analysis system 104.

In some examples, the user application 210 provides instructions on how to perform the test (e.g., how to obtain the sample, how to apply the sample to the test strip 604, etc.). The user is instructed to perform the test and wait a certain amount of time (e.g., 15 minutes) for the results. When the test is complete, the user takes a picture of the test strip 604 using the camera 208 on the electronic device 102. In some examples, such as shown in FIG. 9, the user application 210 displays one or more guides or frames to help center the test strip 604 in the image. The user may press a button or issue a voice command to capture the image 602. After the image 602 is captured, the user application 210 transmits the image 602 to the image analysis system 104. The image analysis system 104 determines the result and transmits the result back to the user application 210. In some examples, the image analysis system 104 transmits (reports) the result to a disease tracker, such as a public health agency.

The user application 210 displays the results, such as shown in FIGS. 5O, 5P, 5Q. If the result was invalid, the user can try to resubmit the same image 602 or take another image of the test strip 604 and submit the new image to the image analysis system 104. In some examples, the user application 210 does not provide the ability to override the image analysis. Therefore, once the image is taken and sent to the image analysis system 104, the user cannot override the analysis or change the result. However, in some examples, the user application 210 may enable the user to submit or report an issue. The example process disclosed above results in simplified post-test instructions, faster and more accurate test result interpretation, and potential for semi-validated test results (e.g., since the result is associated with the user that submitted the result, but not able to verify the sample belonged to the same user).

While an example manner of implementing the analyzer circuitry 300 is illustrated in FIG. 3, one or more of the elements, processes, and/or devices illustrated in FIG. 3 may be combined, divided, re-arranged, omitted, eliminated, and/or implemented in any other way. Further, the example format verifier circuitry 306, the example authenticator circuitry 308, the example position detector circuitry 310, the example result detection circuitry 312, the example secondary model circuitry 314, the example performance monitor circuitry 316, the model adjuster 318, and/or, more generally, the example analyzer circuitry 300 of FIG. 3, may be implemented by hardware, software, firmware, and/or any combination of hardware, software, and/or firmware. Thus, for example, any of the example format verifier circuitry 306, the example authenticator circuitry 308, the example position detector circuitry 310, the example result detection circuitry 312, the example secondary model circuitry 314, the example performance monitor circuitry 316, the model adjuster 318, and/or, more generally, the example analyzer circuitry 300, could be implemented by processor circuitry, analog circuit(s), digital circuit(s), logic circuit(s), programmable processor(s), programmable microcontroller(s), graphics processing unit(s) (GPU(s)), digital signal processor(s) (DSP(s)), application specific integrated circuit(s) (ASIC(s)), programmable logic device(s) (PLD(s)), and/or field programmable logic device(s) (FPLD(s)) such as Field Programmable Gate Arrays (FPGAs). When reading any of the apparatus or system claims of this patent to cover a purely software and/or firmware implementation, at least one of the example format verifier circuitry 306, the example authenticator circuitry 308, the example position detector circuitry 310, the example result detection circuitry 312, the example secondary model circuitry 314, the example performance monitor circuitry 316, and/or the model adjuster 318 is/are hereby expressly defined to include a non-transitory computer readable storage device or storage disk such as a memory, a digital versatile disk (DVD), a compact disk (CD), a Blu-ray disk, etc., including the software and/or firmware. Further still, the example analyzer circuitry 300 of FIG. 3 may include one or more elements, processes, and/or devices in addition to, or instead of, those illustrated in FIG. 3, and/or may include more than one of any or all of the illustrated elements, processes and devices.

Figure 10A:
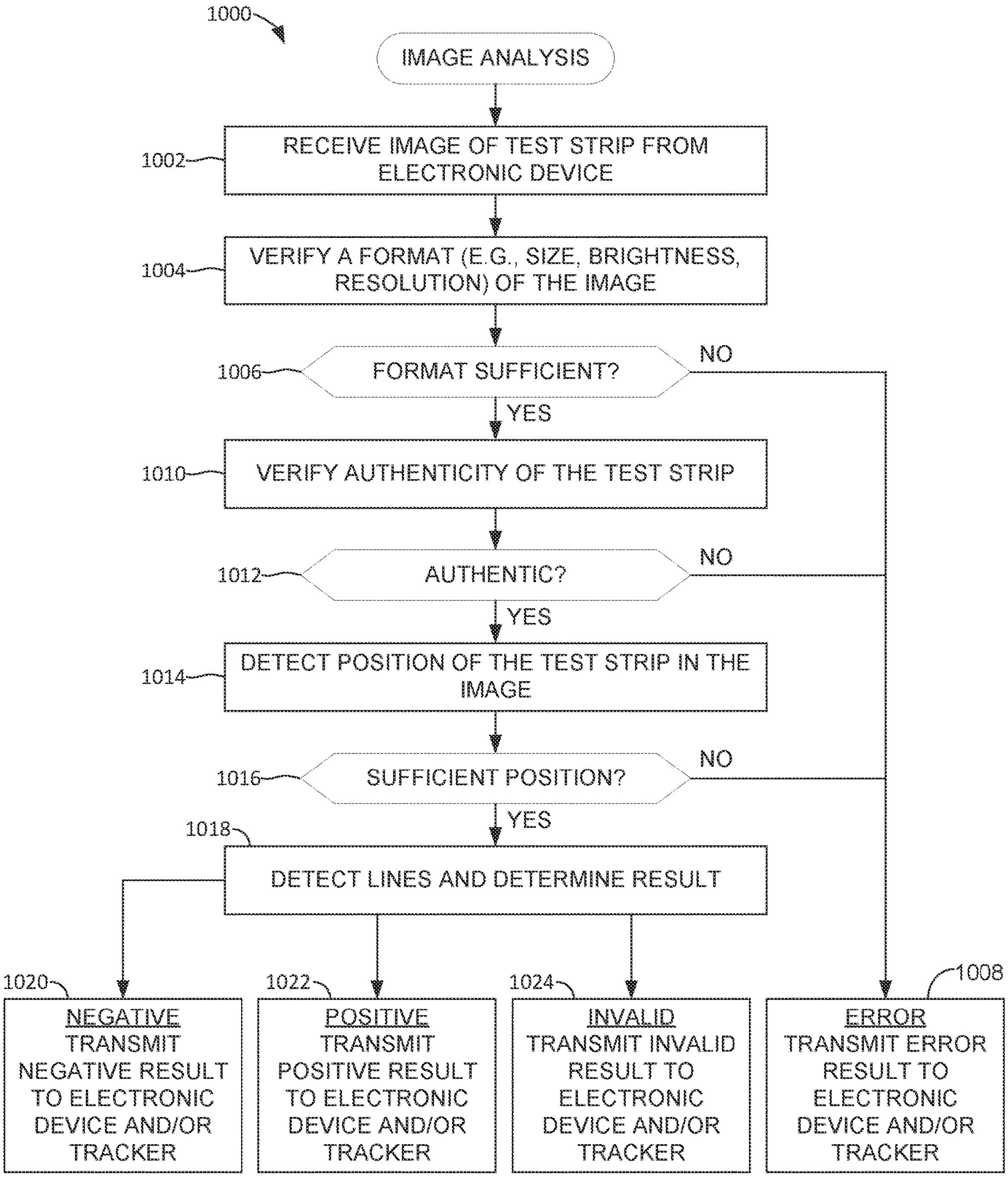
FIGS. 10A and 10B are flowcharts representative of example machine readable instructions that may be executed by example processor circuitry to implement example analyzer circuitry of the example image analysis system of FIGS. 1 and 3.
Figure 10B:
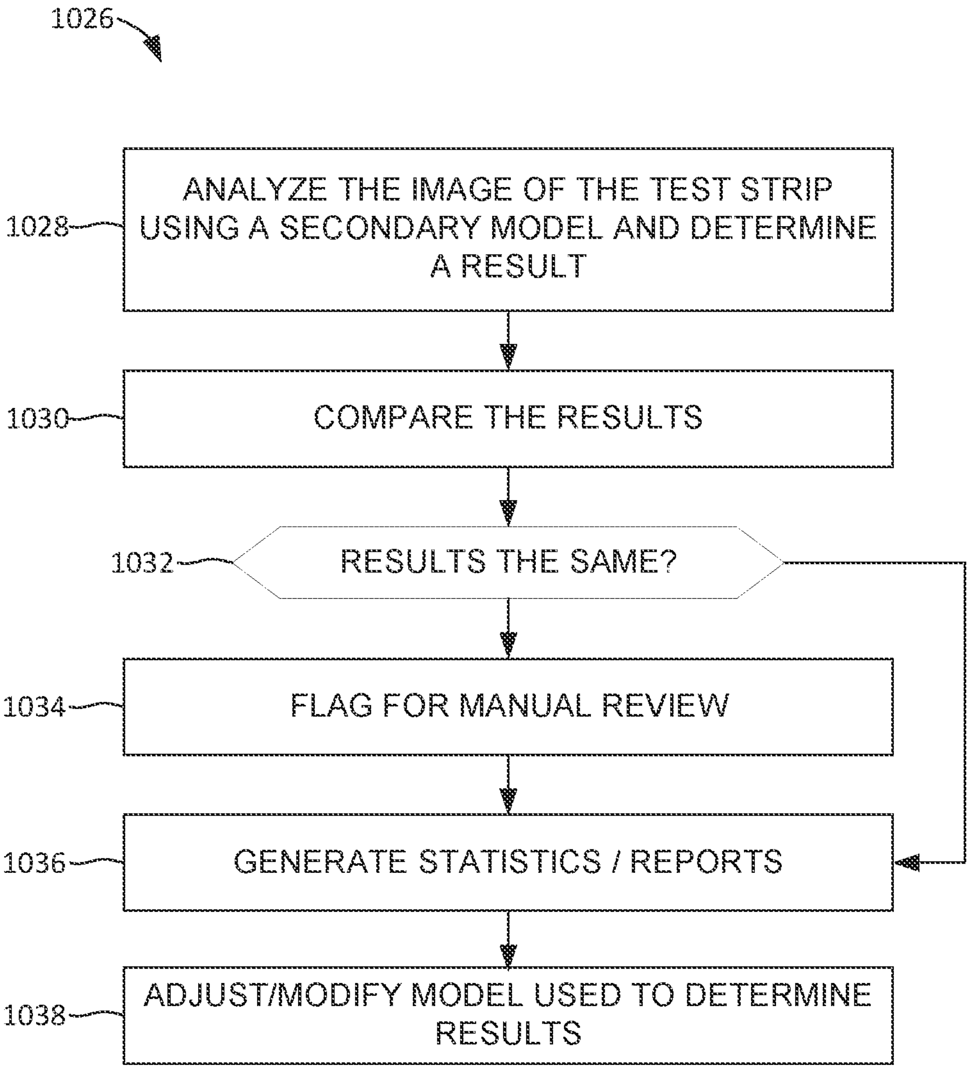

Flowcharts representative of example hardware logic circuitry, machine readable instructions, hardware implemented state machines, and/or any combination thereof for implementing the analyzer circuitry 300 of FIG. 3 are shown in FIGS. 10A and 10B. The machine readable instructions may be one or more executable programs or portion(s) of an executable program for execution by processor circuitry, such as the processor circuitry 1112 shown in the example processor platform 1100 discussed below in connection with FIG. 11 and/or the example processor circuitry discussed below in connection with FIGS. 12 and/or 13. The program may be embodied in software stored on one or more non-transitory computer readable storage media such as a CD, a floppy disk, a hard disk drive (HDD), a DVD, a Blu-ray disk, a volatile memory (e.g., Random Access Memory (RAM) of any type, etc.), or a non-volatile memory (e.g., FLASH memory, an HDD, etc.) associated with processor circuitry located in one or more hardware devices, but the entire program and/or parts thereof could alternatively be executed by one or more hardware devices other than the processor circuitry and/or embodied in firmware or dedicated hardware. The machine readable instructions may be distributed across multiple hardware devices and/or executed by two or more hardware devices (e.g., a server and a client hardware device). For example, the client hardware device may be implemented by an endpoint client hardware device (e.g., a hardware device associated with a user) or an intermediate client hardware device (e.g., a radio access network (RAN) gateway that may facilitate communication between a server and an endpoint client hardware device). Similarly, the non-transitory computer readable storage media may include one or more mediums located in one or more hardware devices. Further, although the example programs is/are described with reference to the flowcharts illustrated in FIGS. 10A and 10B, many other methods of implementing the example analyzer circuitry 300 may alternatively be used. For example, the order of execution of the blocks may be changed, and/or some of the blocks described may be changed, eliminated, or combined. Additionally or alternatively, any or all of the blocks may be implemented by one or more hardware circuits (e.g., processor circuitry, discrete and/or integrated analog and/or digital circuitry, an FPGA, an ASIC, a comparator, an operational-amplifier (op-amp), a logic circuit, etc.) structured to perform the corresponding operation without executing software or firmware. The processor circuitry may be distributed in different network locations and/or local to one or more hardware devices (e.g., a single-core processor (e.g., a single core central processor unit (CPU)), a multi-core processor (e.g., a multi-core CPU), etc.) in a single machine, multiple processors distributed across multiple servers of a server rack, multiple processors distributed across one or more server racks, a CPU and/or a FPGA located in the same package (e.g., the same integrated circuit (IC) package or in two or more separate housings, etc.).

The machine readable instructions described herein may be stored in one or more of a compressed format, an encrypted format, a fragmented format, a compiled format, an executable format, a packaged format, etc. Machine readable instructions as described herein may be stored as data or a data structure (e.g., as portions of instructions, code, representations of code, etc.) that may be utilized to create, manufacture, and/or produce machine executable instructions. For example, the machine readable instructions may be fragmented and stored on one or more storage devices and/or computing devices (e.g., servers) located at the same or different locations of a network or collection of networks (e.g., in the cloud, in edge devices, etc.). The machine readable instructions may require one or more of installation, modification, adaptation, updating, combining, supplementing, configuring, decryption, decompression, unpacking, distribution, reassignment, compilation, etc., in order to make them directly readable, interpretable, and/or executable by a computing device and/or other machine. For example, the machine readable instructions may be stored in multiple parts, which are individually compressed, encrypted, and/or stored on separate computing devices, wherein the parts when decrypted, decompressed, and/or combined form a set of machine executable instructions that implement one or more operations that may together form a program such as that described herein.

In another example, the machine readable instructions may be stored in a state in which they may be read by processor circuitry, but require addition of a library (e.g., a dynamic link library (DLL)), a software development kit (SDK), an application programming interface (API), etc., in order to execute the machine readable instructions on a particular computing device or other device. In another example, the machine readable instructions may need to be configured (e.g., settings stored, data input, network addresses recorded, etc.) before the machine readable instructions and/or the corresponding program(s) can be executed in whole or in part. Thus, machine readable media, as used herein, may include machine readable instructions and/or program(s) regardless of the particular format or state of the machine readable instructions and/or program(s) when stored or otherwise at rest or in transit.

The machine readable instructions described herein can be represented by any past, present, or future instruction language, scripting language, programming language, etc. For example, the machine readable instructions may be represented using any of the following languages: C, C++, Java, C#, Perl, Python, JavaScript, HyperText Markup Language (HTML), Structured Query Language (SQL), Swift, etc.

As mentioned above, the example operations of FIG. 6 may be implemented using executable instructions (e.g., computer and/or machine readable instructions) stored on one or more non-transitory computer and/or machine readable media such as optical storage devices, magnetic storage devices, an HDD, a flash memory, a read-only memory (ROM), a CD, a DVD, a cache, a RAM of any type, a register, and/or any other storage device or storage disk in which information is stored for any duration (e.g., for extended time periods, permanently, for brief instances, for temporarily buffering, and/or for caching of the information). As used herein, the terms non-transitory computer readable medium and non-transitory computer readable storage medium is expressly defined to include any type of computer readable storage device and/or storage disk and to exclude propagating signals and to exclude transmission media.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc., may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, or (7) A with B and with C. As used herein in the context of describing structures, components, items, objects and/or things, the phrase "at least one of A and B" is intended to refer to implementations including any of (1) at least one A, (2) at least one B, or (3) at least one A and at least one B. Similarly, as used herein in the context of describing structures, components, items, objects and/or things, the phrase "at least one of A or B" is intended to refer to implementations including any of (1) at least one A, (2) at least one B, or (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, or (3) at least one A and at least one B. Similarly, as used herein in the context of describing the performance or execution of processes, instructions, actions, activities and/or steps, the phrase "at least one of A or B" is intended to refer to implementations including any of (1) at least one A, (2) at least one B, or (3) at least one A and at least one B.

As used herein, singular references (e.g., "a", "an", "first", "second", etc.) do not exclude a plurality. The term "a" or "an" object, as used herein, refers to one or more of that object. The terms "a" (or "an"), "one or more", and "at least one" are used interchangeably herein. Furthermore, although individually listed, a plurality of means, elements or method actions may be implemented by, e.g., the same entity or object. Additionally, although individual features may be included in different examples or claims, these may possibly be combined, and the inclusion in different examples or claims does not imply that a combination of features is not feasible and/or advantageous.

FIG. 10A is a flowchart representative of example machine readable instructions and/or example operations 1000 that may be executed and/or instantiated by processor circuitry to analyze an image of a test strip. The example machine readable instructions and/or operations 1000 are described in connection with the process disclosed in FIG. 4 with the image 402 of the test strip 106, but can be similarly performed in connection with the process disclosed in FIG. 6 with the image 602 of the test strip 604. The machine readable instructions and/or operations 1000 of FIG. 10A begin at block 1002, at which the analyzer circuitry 300 receives the image 402 from the electronic device 102.

At block 1004, the format verifier circuitry 306 verifies the image 402 has sufficient format. For example, the format verifier circuitry 306 may check the size of the image 402 (e.g., for a certain pixel area), the resolution of the image 402, the brightness of the image 402, etc. At block 1006, the format verifier circuitry 306 determines whether the format of the image 402 is sufficient. In some examples, the format verifier circuitry 306 compares one or more parameters or parameter values of the image 402 to one or more thresholds. If the parameter(s)/parameter value(s) satisfy the threshold(s), the image form is sufficient and control proceeds to block 1010. If the parameter(s)/parameter value(s) fail the threshold(s), the image format is insufficient. If the format is insufficient, the format verifier circuitry 306, at block 1008, generates an error result. In some examples, the format verifier circuitry 306 saves the error result with the image 402 in the memory 302. In some examples, the format verifier circuitry 306 transmits the error result to the electronic device 102 and/or the disease tracker(s) 108.

At block 1010, the authenticator circuitry 308 verifies or checks the authenticity of the test strip 106. In some examples, the authenticator circuitry 308 perform an OCR process and searches for a target text in the image 402, such as a brand, type, manufacturer name, and/or code on the test strip 106. In some examples, the authenticator circuitry 308 implements and/or executes a machine learning model to perform the OCR process on the image 402. The machine learning model may be pre-trained. In some examples, the machine learning model is a CNN model. In other examples, other types of machine learning models can be implemented.

At block 1012, the authenticator circuitry 308 determines whether the test strip 106 is authentic based on whether the target text was identified. If the authenticator circuitry 308 identified the target text, control proceeds to block 1014. If the authenticator circuitry 308 did not identify the target text, the authenticator circuitry 308, at block 608, generates an error result. In some examples, the authenticator circuitry 308 saves the error result with the image 402 in the memory 302. In some examples, the authenticator circuitry 308 transmits the error result to the electronic device 102 and/or the disease tracker(s) 108. In other examples, such as disclosed in connection with FIG. 6, the authenticator circuitry 308 authenticates the test strip by analyzing the image for a machine readable code on the test strip (e.g., the machine readable code 700). In some examples, the authenticator circuitry 308 detects and interprets the machine readable code to obtain a serial number, which the authenticator circuitry 308 compares to a list of serial numbers to ensure the test strip is still valid.

At block 1014, the position detector circuitry 310 detects the position (e.g., orientation or angle) of the test strip 106 in the image 402. For example, the position detector circuitry 310 can determine the angle of the test strip 106 relative to a vertical alignment and/or relative to a different baseline alignment. At block 1016, the position detector circuitry 310 determines whether the position is sufficient. In some examples, the position detector circuitry 310 compares the angle of the test strip 106 relative to a threshold angle or range (e.g., ±10° from vertical). If the position detector circuitry 310 determines the angle satisfies the threshold (e.g., is within or less than the threshold), control proceeds to block 1018. If the position detector circuitry 310 determines the angle does not satisfy the threshold (e.g., is outside or greater than the threshold), the position detector circuitry 310, at block 1008, generates an error result. In some examples, the position detector circuitry 310 saves the error result with the image 402 in the memory 302. In some examples, the position detector circuitry 310 transmits the error result to the electronic device 102 and/or the disease tracker(s) 108. In other examples, as disclosed in connection with FIG. 6, the position detector circuitry 310 may identify a sub-region 802 of the image corresponding to the test region based on a location, orientation, and/or size of the machine readable code.

At block 1018, the result detection circuitry 312 analyzes the image to detect the test region and interpret the lines. In some examples, the result detection circuitry 312 implements and/or executes a machine learning model to analyze the image and detect the line(s). Based on the lines, the result detection circuitry 312 determines whether the result is negative or positive. If the result is negative, the result detection circuitry 312, at block 1020, generates a negative result notification. If the result is positive, the result detection circuitry 312, at block 1022, generates a positive result notification. If the result detection circuitry 312 was unable to determine the result, the result detection circuitry 312, at block 1024, generates an invalid result notification. In some examples, the result detection circuitry 312 saves the result with the image 402 in the memory 302. In some examples, the result detection circuitry 312 transmits the result to the electronic device 102 and/or the disease tracker(s) 108. In some examples, in response to an error or invalid result, the user can take an additional image of the test strip and submit the additional new image to the image analysis system 104.

In some examples, as disclosed above in connection with the process in FIG. 6, the result can be compared to a result from another process. For example, FIG. 10B is a flowchart representative of example machine readable instructions and/or example operations 1026 that may be executed and/or instantiated by processor circuitry. In some examples, the example machine readable instructions and/or example operations 1026 may be performed after the example machine readable instructions and/or example operations 1000 of FIG. 10A. At block 1028, the secondary model circuitry 314 analyzes the image of the test strip using a secondary model, such as a machine learning model that is different the machine learning model implemented at block 1018, and determines a result of the test. This operation may be performed independently of the operation performed in block 1018. The operations may be performed simultaneously or in a certain order. At block 1030, the performance monitor circuitry 316 compares the result from the detection circuitry 312 (at block 1018) and the result from the secondary model circuitry 314 (at block 1030). At block 1032, the performance monitor circuitry 316 determines if the results are the same. If the results are not the same, the performance monitor circuitry 316, at block 1034, can flag the image for manual review, such that a person can review the image and make a determination of the result. In some examples, the person can manually enter the result, which is then transmitted to the user application 210. At block 1036, the performance monitor circuitry 316 can generate statistics and/or reports, such as how often the results are the same, different, etc.

At block 1038, the model adjuster 318 adjusts or modifies the machine learning model used to determine results. For example, the model adjuster 318 can adjust the machine learning model implemented by the result detection circuitry 312. In some examples, the model adjuster 318 adjusts the machine learning model based on the statistics or comparisons of the results from the two models. The example process in FIG. 10B can be repeated such as, for example, each time a new image is analyzed.

FIG. 11 is a block diagram of an example processor platform 1100 structured to execute and/or instantiate the machine readable instructions and/or operations of FIGS. 10A and 10B to implement the analyzer circuitry 300 of FIG. 3. The processor platform 1100 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, or any other type of computing device.

The processor platform 1100 of the illustrated example includes processor circuitry 1112. The processor circuitry 1112 of the illustrated example is hardware. For example, the processor circuitry 1112 can be implemented by one or more integrated circuits, logic circuits, FPGAs microprocessors, CPUs, GPUs, DSPs, and/or microcontrollers from any desired family or manufacturer. The processor circuitry 1112 may be implemented by one or more semiconductor based (e.g., silicon based) devices. In this example, the processor circuitry 1112 implements the example format verifier circuitry 306, the example authenticator circuitry 308, the example position detector circuitry 310, the example result detection circuitry 312, the secondary model circuitry 314, the performance monitor circuitry 316, the model adjuster 318, and/or, more generally, the example analyzer circuitry 300.

The processor circuitry 1112 of the illustrated example includes a local memory 1113 (e.g., a cache, registers, etc.). The processor circuitry 1112 of the illustrated example is in communication with a main memory including a volatile memory 1114 and a non-volatile memory 1116 by a bus 1118. The volatile memory 1114 may be implemented by Synchronous Dynamic Random Access Memory (SDRAM), Dynamic Random Access Memory (DRAM), RAMBUS® Dynamic Random Access Memory (RDRAM®), and/or any other type of RAM device. The non-volatile memory 1116 may be implemented by flash memory and/or any other desired type of memory device. Access to the main memory 1114, 1116 of the illustrated example is controlled by a memory controller 1117. In this example, the memory 302 is implemented by the local memory 1113. However, in other examples, the memory 302 can be implemented in another memory of the processor platform 1100.

The processor platform 1100 of the illustrated example also includes interface circuitry 1120. The interface circuitry 1120 may be implemented by hardware in accordance with any type of interface standard, such as an Ethernet interface, a universal serial bus (USB) interface, a Bluetooth® interface, a near field communication (NFC) interface, a PCI interface, and/or a PCIe interface.

In the illustrated example, one or more input devices 1122 are connected to the interface circuitry 1120. The input device(s) 1122 permit(s) a user to enter data and/or commands into the processor circuitry 1112. The input device(s) 1122 can be implemented by, for example, an audio sensor, a microphone, a camera (still or video), a keyboard, a button, a mouse, a touchscreen, a track-pad, a trackball, an isopoint device, and/or a voice recognition system.

One or more output devices 1124 are also connected to the interface circuitry 1120 of the illustrated example. The output devices 1124 can be implemented, for example, by display devices (e.g., a light emitting diode (LED), an organic light emitting diode (OLED), a liquid crystal display (LCD), a cathode ray tube (CRT) display, an in-place switching (IPS) display, a touchscreen, etc.), a tactile output device, a printer, and/or speaker. The interface circuitry 1120 of the illustrated example, thus, typically includes a graphics driver card, a graphics driver chip, and/or graphics processor circuitry such as a GPU.

The interface circuitry 1120 of the illustrated example also includes a communication device such as a transmitter, a receiver, a transceiver (e.g., the transceiver 304), a modem, a residential gateway, a wireless access point, and/or a network interface to facilitate exchange of data with external machines (e.g., computing devices of any kind) by a network 1126. The communication can be by, for example, an Ethernet connection, a digital subscriber line (DSL) connection, a telephone line connection, a coaxial cable system, a satellite system, a line-of-site wireless system, a cellular telephone system, an optical connection, etc.

The processor platform 1100 of the illustrated example also includes one or more mass storage devices 1128 to store software and/or data. Examples of such mass storage devices 1128 include magnetic storage devices, optical storage devices, floppy disk drives, HDDs, CDs, Blu-ray disk drives, redundant array of independent disks (RAID) systems, solid state storage devices such as flash memory devices, and DVD drives.

The machine executable instructions 1132, which may be implemented by the machine readable instructions of FIGS.

10A and 10B, may be stored in the mass storage device 1128, in the volatile memory 1114, in the non-volatile memory 1116, and/or on a removable non-transitory computer readable storage medium such as a CD or DVD.

Figure 12:
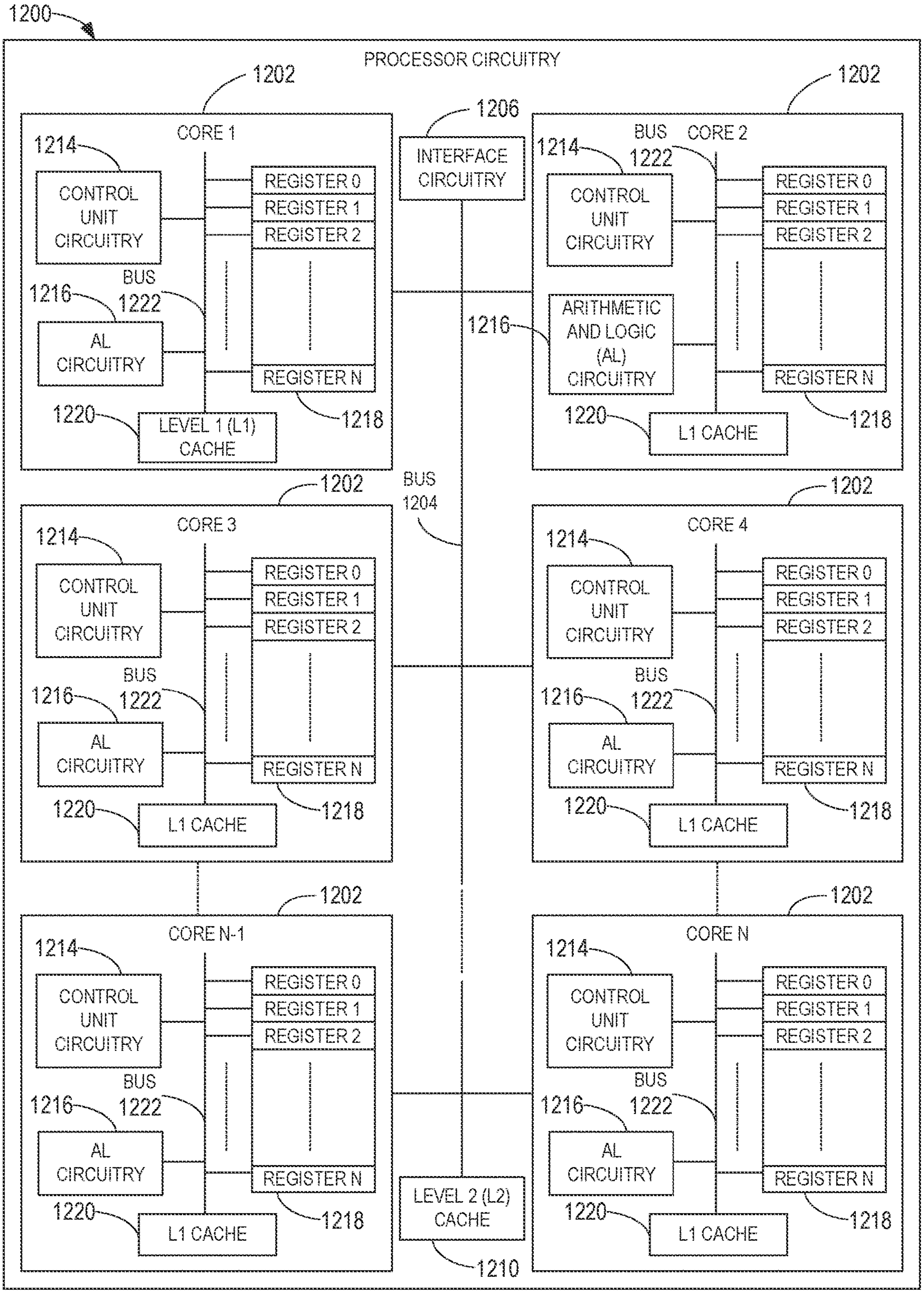
FIG. 12 is a block diagram of an example implementation of the processor circuitry of FIG. 11.

FIG. 12 is a block diagram of an example implementation of the processor circuitry 1112 of FIG. 11. In this example, the processor circuitry 1112 of FIG. 11 is implemented by a microprocessor 1200. For example, the microprocessor 1200 may implement multi-core hardware circuitry such as a CPU, a DSP, a GPU, an XPU, etc. Although it may include any number of example cores 802 (e.g., 1 core), the microprocessor 1200 of this example is a multi-core semiconductor device including N cores. The cores 1202 of the microprocessor 1200 may operate independently or may cooperate to execute machine readable instructions. For example, machine code corresponding to a firmware program, an embedded software program, or a software program may be executed by one of the cores 1202 or may be executed by multiple ones of the cores 1202 at the same or different times. In some examples, the machine code corresponding to the firmware program, the embedded software program, or the software program is split into threads and executed in parallel by two or more of the cores 1202. The software program may correspond to a portion or all of the machine readable instructions and/or operations represented by the flowcharts of FIGS. 10A and 10B.

The cores 1202 may communicate by an example bus 1204. In some examples, the bus 1204 may implement a communication bus to effectuate communication associated with one(s) of the cores 1202. For example, the bus 1204 may implement at least one of an Inter-Integrated Circuit (I2C) bus, a Serial Peripheral Interface (SPI) bus, a PCI bus, or a PCIe bus. Additionally or alternatively, the bus 1204 may implement any other type of computing or electrical bus. The cores 1202 may obtain data, instructions, and/or signals from one or more external devices by example interface circuitry 1206. The cores 1202 may output data, instructions, and/or signals to the one or more external devices by the interface circuitry 1206. Although the cores 1202 of this example include example local memory 1220 (e.g., Level 1 (L1) cache that may be split into an L1 data cache and an L1 instruction cache), the microprocessor 1200 also includes example shared memory 1210 that may be shared by the cores (e.g., Level 2 (L2_cache)) for high-speed access to data and/or instructions. Data and/or instructions may be transferred (e.g., shared) by writing to and/or reading from the shared memory 1210. The local memory 1220 of each of the cores 1202 and the shared memory 1210 may be part of a hierarchy of storage devices including multiple levels of cache memory and the main memory (e.g., the main memory 1114, 1116 of FIG. 11). Typically, higher levels of memory in the hierarchy exhibit lower access time and have smaller storage capacity than lower levels of memory. Changes in the various levels of the cache hierarchy are managed (e.g., coordinated) by a cache coherency policy.

Each core 1202 may be referred to as a CPU, DSP, GPU, etc., or any other type of hardware circuitry. Each core 1202 includes control unit circuitry 1214, arithmetic and logic (AL) circuitry (sometimes referred to as an ALU) 1216, a plurality of registers 1218, the L1 cache 1220, and an example bus 1222. Other structures may be present. For example, each core 1202 may include vector unit circuitry, single instruction multiple data (SIMD) unit circuitry, load/store unit (LSU) circuitry, branch/jump unit circuitry, floating-point unit (FPU) circuitry, etc. The control unit circuitry 1214 includes semiconductor-based circuits structured to control (e.g., coordinate) data movement within the corresponding core 1202. The AL circuitry 1216 includes semiconductor-based circuits structured to perform one or more mathematic and/or logic operations on the data within the corresponding core 1202. The AL circuitry 1216 of some examples performs integer based operations. In other examples, the AL circuitry 1216 also performs floating point operations. In yet other examples, the AL circuitry 1216 may include first AL circuitry that performs integer based operations and second AL circuitry that performs floating point operations. In some examples, the AL circuitry 1216 may be referred to as an Arithmetic Logic Unit (ALU). The registers 1218 are semiconductor-based structures to store data and/or instructions such as results of one or more of the operations performed by the AL circuitry 1216 of the corresponding core 1202. For example, the registers 1218 may include vector register(s), SIMD register(s), general purpose register(s), flag register(s), segment register(s), machine specific register(s), instruction pointer register(s), control register(s), debug register(s), memory management register(s), machine check register(s), etc. The registers 1218 may be arranged in a bank as shown in FIG. 12. Alternatively, the registers 1218 may be organized in any other arrangement, format, or structure including distributed throughout the core 1202 to shorten access time. The bus 1222 may implement at least one of an I2C bus, a SPI bus, a PCI bus, or a PCIe bus.

Each core 1202 and/or, more generally, the microprocessor 1200 may include additional and/or alternate structures to those shown and described above. For example, one or more clock circuits, one or more power supplies, one or more power gates, one or more cache home agents (CHAs), one or more converged/common mesh stops (CMSs), one or more shifters (e.g., barrel shifter(s)) and/or other circuitry may be present. The microprocessor 1200 is a semiconductor device fabricated to include many transistors interconnected to implement the structures described above in one or more integrated circuits (ICs) contained in one or more packages. The processor circuitry may include and/or cooperate with one or more accelerators. In some examples, accelerators are implemented by logic circuitry to perform certain tasks more quickly and/or efficiently than can be done by a general purpose processor. Examples of accelerators include ASICs and FPGAs such as those discussed herein. A GPU or other programmable device can also be an accelerator. Accelerators may be on-board the processor circuitry, in the same chip package as the processor circuitry and/or in one or more separate packages from the processor circuitry.

Figure 13:
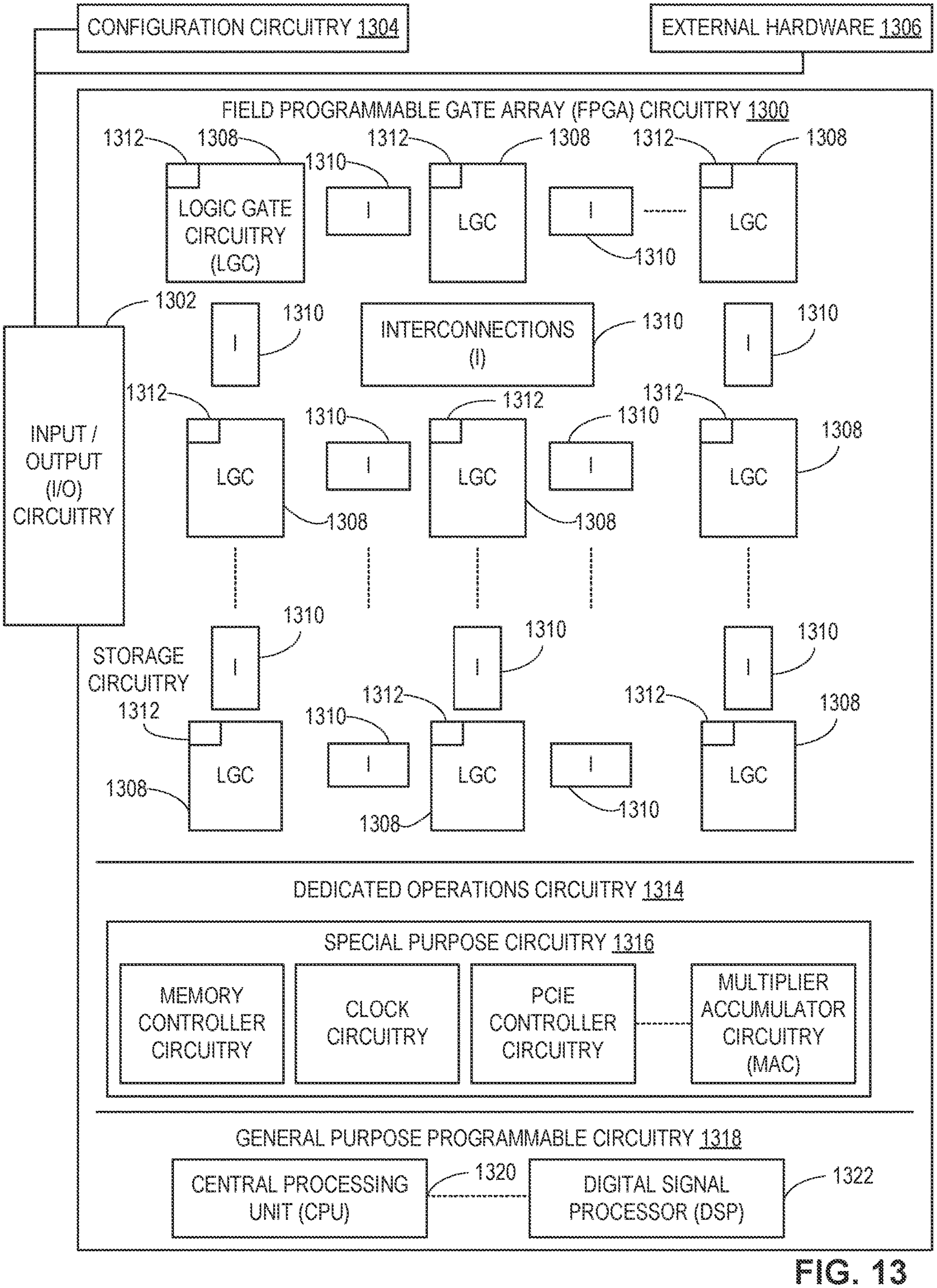
FIG. 13 is a block diagram of another example implementation of the processor circuitry of FIG. 11.

FIG. 13 is a block diagram of another example implementation of the processor circuitry 1112 of FIG. 11. In this example, the processor circuitry 1312 is implemented by FPGA circuitry 1300. The FPGA circuitry 1300 can be used, for example, to perform operations that could otherwise be performed by the example microprocessor 1200 of FIG. 12 executing corresponding machine readable instructions. However, once configured, the FPGA circuitry 1300 instantiates the machine readable instructions in hardware and, thus, can often execute the operations faster than they could be performed by a general purpose microprocessor executing the corresponding software.

More specifically, in contrast to the microprocessor 1200 of FIG. 12 described above (which is a general purpose device that may be programmed to execute some or all of the machine readable instructions represented by the flowcharts of FIGS. 10A and 10B but whose interconnections and logic circuitry are fixed once fabricated), the FPGA circuitry 1300 of the example of FIG. 13 includes interconnections and logic circuitry that may be configured and/or interconnected in different ways after fabrication to instantiate, for example, some or all of the machine readable instructions represented by the flowcharts of FIGS. 10A and 10B. In particular, the FPGA 1300 may be thought of as an array of logic gates, interconnections, and switches. The switches can be programmed to change how the logic gates are interconnected by the interconnections, effectively forming one or more dedicated logic circuits (unless and until the FPGA circuitry 1300 is reprogrammed). The configured logic circuits enable the logic gates to cooperate in different ways to perform different operations on data received by input circuitry. Those operations may correspond to some or all of the software represented by the flowcharts of FIGS. 10A and 10B. As such, the FPGA circuitry 1300 may be structured to effectively instantiate some or all of the machine readable instructions of the flowcharts of FIGS. 10A and 10B as dedicated logic circuits to perform the operations corresponding to those software instructions in a dedicated manner analogous to an ASIC. Therefore, the FPGA circuitry 1300 may perform the operations corresponding to the some or all of the machine readable instructions of FIGS. 10A and 10B faster than the general purpose microprocessor can execute the same.

In the example of FIG. 13, the FPGA circuitry 1300 is structured to be programmed (and/or reprogrammed one or more times) by an end user by a hardware description language (HDL) such as Verilog. The FPGA circuitry 1300 of FIG. 13, includes example input/output (I/O) circuitry 1302 to obtain and/or output data to/from example configuration circuitry 1304 and/or external hardware (e.g., external hardware circuitry) 1306. For example, the configuration circuitry 1304 may implement interface circuitry that may obtain machine readable instructions to configure the FPGA circuitry 1300, or portion(s) thereof. In some such examples, the configuration circuitry 1304 may obtain the machine readable instructions from a user, a machine (e.g., hardware circuitry (e.g., programmed or dedicated circuitry) that may implement an Artificial Intelligence/Machine Learning (AI/ML) model to generate the instructions), etc. In some examples, the external hardware 1306 may implement the microprocessor 1200 of FIG. 12. The FPGA circuitry 1300 also includes an array of example logic gate circuitry 1308, a plurality of example configurable interconnections 1310, and example storage circuitry 1312. The logic gate circuitry 1308 and interconnections 1310 are configurable to instantiate one or more operations that may correspond to at least some of the machine readable instructions of FIGS. 10A and 10B and/or other desired operations. The logic gate circuitry 1308 shown in FIG. 13 is fabricated in groups or blocks. Each block includes semiconductor-based electrical structures that may be configured into logic circuits. In some examples, the electrical structures include logic gates (e.g., And gates, Or gates, Nor gates, etc.) that provide basic building blocks for logic circuits. Electrically controllable switches (e.g., transistors) are present within each of the logic gate circuitry 1308 to enable configuration of the electrical structures and/or the logic gates to form circuits to perform desired operations. The logic gate circuitry 1308 may include other electrical structures such as look-up tables (LUTs), registers (e.g., flip-flops or latches), multiplexers, etc.

The interconnections 1310 of the illustrated example are conductive pathways, traces, vias, or the like that may include electrically controllable switches (e.g., transistors) whose state can be changed by programming (e.g., using an HDL instruction language) to activate or deactivate one or more connections between one or more of the logic gate circuitry 1308 to program desired logic circuits.

The storage circuitry 1312 of the illustrated example is structured to store result(s) of the one or more of the operations performed by corresponding logic gates. The storage circuitry 1312 may be implemented by registers or the like. In the illustrated example, the storage circuitry 1312 is distributed amongst the logic gate circuitry 1308 to facilitate access and increase execution speed.

The example FPGA circuitry 1300 of FIG. 13 also includes example Dedicated Operations Circuitry 1314. In this example, the Dedicated Operations Circuitry 914 includes special purpose circuitry 1316 that may be invoked to implement commonly used functions to avoid the need to program those functions in the field. Examples of such special purpose circuitry 1316 include memory (e.g., DRAM) controller circuitry, PCIe controller circuitry, clock circuitry, transceiver circuitry, memory, and multiplier-accumulator circuitry. Other types of special purpose circuitry may be present. In some examples, the FPGA circuitry 1300 may also include example general purpose programmable circuitry 1318 such as an example CPU 1320 and/or an example DSP 1322. Other general purpose programmable circuitry 1318 may additionally or alternatively be present such as a GPU, an XPU, etc., that can be programmed to perform other operations.

Although FIGS. 12 and 13 illustrate two example implementations of the processor circuitry 1112 of FIG. 11, many other approaches are contemplated. For example, as mentioned above, modern FPGA circuitry may include an on-board CPU, such as one or more of the example CPU 1320 of FIG. 13. Therefore, the processor circuitry 1112 of FIG. 11 may additionally be implemented by combining the example microprocessor 1200 of FIG. 12 and the example FPGA circuitry 1300 of FIG. 13. In some such hybrid examples, a first portion of the machine readable instructions represented by the flowcharts of FIGS. 10A and 10B may be executed by one or more of the cores 1202 of FIG. 12 and a second portion of the machine readable instructions represented by the flowchart of FIGS. 10A and 10B may be executed by the FPGA circuitry 1300 of FIG. 13.

In some examples, the processor circuitry 1112 of FIG. 11 may be in one or more packages. For example, the processor circuitry 1200 of FIG. 12 and/or the FPGA circuitry 1300 of FIG. 13 may be in one or more packages. In some examples, an XPU may be implemented by the processor circuitry 1112 of FIG. 11, which may be in one or more packages. For example, the XPU may include a CPU in one package, a DSP in another package, a GPU in yet another package, and an FPGA in still yet another package.

Figure 14:
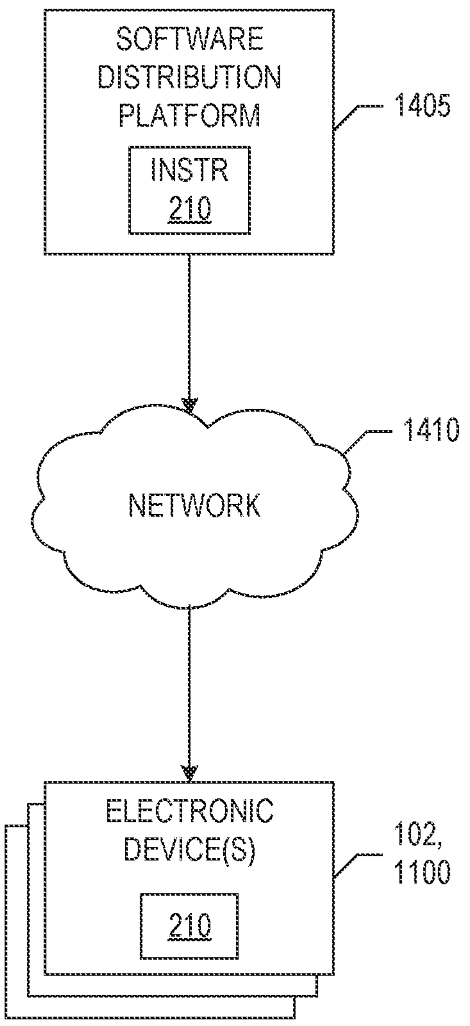
FIG. 14 is a block diagram of an example software distribution platform (e.g., one or more servers) to distribute software to client devices associated with end users and/or consumers (e.g., for license, sale, and/or use), retailers (e.g., for sale, re-sale, license, and/or sub-license), and/or original equipment manufacturers (OEMs) (e.g., for inclusion in products to be distributed to, for example, retailers and/or to other end users such as direct buy customers).

A block diagram illustrating an example software distribution platform 1405 to distribute software such as the example user application 210 to hardware devices owned and/or operated by third parties is illustrated in FIG. 14. As disclosed above, in some examples, one or more aspects of the image analysis system 104 may be incorporated into the user application 210. Thus, one or more steps in the example instructions of FIGS. 10A and 10B also may be incorporated into the user application 210. The example software distribution platform 1405 may be implemented by any computer server, data facility, cloud service, etc., capable of storing and transmitting software (e.g., instructions) to other computing devices (which may be referred to as networked devices). The software distribution platform 1405 executes instructions (first instructions) to distribute the software (second instructions) to the computing device(s). The third parties may be customers of the entity owning and/or operating the software distribution platform 1405. For example, the entity that owns and/or operates the software distribution platform 1405 may be a developer, a seller, and/or a licensor of software such as the example machine readable instructions 210 of FIG. 14. In some examples, the entity that owns and/or operates the software distribution platform 1405 is the same entity that owns and/or operates the image analysis system 104. The third parties may be consumers, users, retailers, OEMs, etc., who purchase and/or license the software for use and/or re-sale and/or sub-licensing. In the illustrated example, the software distribution platform 1405 includes one or more servers and one or more storage devices. The electronic devices store the machine readable instructions 210. The one or more servers of the example software distribution platform 1405 are in communication with a network 1410, which may correspond to any one or more of the Internet and/or any of the example networks described above. In some examples, the one or more servers are responsive to requests to transmit the software to a requesting party as part of a commercial transaction. Payment for the delivery, sale, and/or license of the software may be handled by the one or more servers of the software distribution platform and/or by a third party payment entity. The servers enable purchasers and/or licensors to download the machine readable instructions 210 from the software distribution platform 1405. For example, the software, may be downloaded to the example processor platform, which is to execute the machine readable instructions 210 to implement the example user application 210. In some example, one or more servers of the software distribution platform 1405 periodically offer, transmit, and/or force updates to the software (e.g., the example machine readable instructions 210) to ensure improvements, patches, updates, etc., are distributed and applied to the software at the end user devices.

From the foregoing, it will be appreciated that example systems, methods, apparatus, and articles of manufacture have been disclosed that can automatically analyze an image of a test strip and interpret the results. The disclosed systems, methods, apparatus, and articles of manufacture execute one or more image analysis operations that improve the efficiency of using a computing device by leveraging machine learning models and reducing computing power by eliminating certain operations when an image fails one of the operations.

Examples and example combinations disclosed herein include the following:

Example 1 is at least one non-transitory computer readable medium comprising instructions that, when executed, cause at least one processor to at least verify a format of an image of a lateral flow assay device. The lateral flow assay device is to implement a diagnostic test to test a sample for a presence or an absence of a target analyte. The lateral flow assay device has a test region to generate a visual indicator representing a result of the diagnostic test. The instructions also cause the at least one processor to verify the lateral flow assay device in the image is authentic by executing a first machine learning model, detect a position of the lateral flow assay device in the image, and analyze the image, by executing a second machine learning model, to determine the result of the diagnostic test.

Example 2 includes the non-transitory computer readable medium of Example 1, wherein the instructions, when executed, cause the at least one processor to execute the first machine learning model to detect a target text in the image.

Example 3 includes the non-transitory computer readable medium of Example 2, wherein the target text includes at least one of a brand, a manufacturer, a code, or a type of the lateral flow assay device.

Example 4 includes the non-transitory computer readable medium of any of Examples 1-3, wherein at least one of the first machine learning model or the second machine learning model is a Convolutional Neural Network (CNN) model.

Example 5 includes the non-transitory computer readable medium of any of Examples 1-4, wherein the second machine learning model is a deep learning model.

Example 6 includes the non-transitory computer readable medium of any of Examples 1-5, wherein the second machine learning model is different than the first machine learning model.

Example 7 includes the non-transitory computer readable medium of any of Examples 1-6, wherein the instructions, when executed, cause the at least one processor to verify the format of the image by comparing one or more parameters of the image to one or more thresholds.

Example 8 includes the non-transitory computer readable medium of Example 7, wherein the instructions, when executed, cause the at least one processor to generate an error result if one or more of the parameters fails the one or more thresholds.

Example 9 includes the non-transitory computer readable medium of Example 8, wherein the one or more parameters includes at least one of image size, resolution, or brightness.

Example 10 includes the non-transitory computer readable medium of any of Examples 1-9, wherein the instructions, when executed, cause the at least one processor to determine an angle of the lateral flow assay device in the image relative to a vertical position, and compare the angle to a threshold range.

Example 11 includes the non-transitory computer readable medium of Example 10, wherein the instructions, when executed, cause the at least one processor to generate an error result if the angle does not satisfy the threshold range.

Example 12 includes the non-transitory computer readable medium of any of Examples 1-11, wherein the result is one of a negative result, a positive result, or an invalid result.

Example 13 includes the non-transitory computer readable medium of any of Examples 1-12, wherein the instructions, when executed, cause the at least one processor to transmit the result to a disease tracker.

Example 14 includes the non-transitory computer readable medium of any of Examples 1-13, wherein the instructions, when executed, cause the at least one processor to transmit the result to an electronic device that obtained the image.

Example 15 includes the non-transitory computer readable medium of any of Examples 1-14, wherein the result is a first result, and wherein the instructions, when executed, cause the at least one processor to analyze the image, using a third machine learning model, to determine a second result of the diagnostic test.

Example 16 includes the non-transitory computer readable medium of Example 15, wherein the instructions, when executed, cause the at least one processor to compare the first result and the second result and at least one of generate a report based on the comparison or adjust the first machine learning model.

Example 17 is an image analysis system comprising at least one memory, instructions in the image analysis system, and processor circuitry to execute the instructions to verify a format of an image of a lateral flow assay device. The lateral flow assay device is to perform a test of a sample for a presence or an absence of a target analyte. The lateral flow assay device has a test region to generate a visual indicator representing a result of the test. The processor circuitry is to verify the lateral flow assay device in the image is authentic by executing a machine learning model to detect a target text on the lateral flow assay device in the image, detect a position of the lateral flow assay device in the image, and analyze the image to determine the result of the test.

Example 18 includes the image analysis system of Example 17, further including a transceiver, wherein the processor circuitry is to execute the instructions to cause the transceiver to transmit the result to a disease tracker.

Example 19 includes the image analysis system of Example 18, wherein the image is obtained by a user electronic device, and wherein the processor circuitry is to execute the instructions to cause the transceiver to transmit the result to the user electronic device.

Example 20 includes the image analysis system of any of Examples 17-19, wherein the machine learning model is a first machine learning model, and wherein the processor circuitry is to analyze the image to determine the result by executing a second machine learning model.

Example 21 includes the image analysis system of Example 20, wherein the second machine learning model is different than the first machine learning model.

Example 22 includes the image analysis system of Examples 20 or 21, wherein at least one of the first machine learning model or the second machine learning model is a Convolutional Neural Network (CNN) model.

Example 23 is a system comprising a server executing first instructions to distribute second instructions to an electronic device including a camera. The second instructions are to guide a user of the electronic device to obtain an image of a lateral flow assay device. The lateral flow assay device is to perform a test of a sample for a presence or an absence of a target analyte. The lateral flow assay has a test region to generate a visual indicator representing a result of the test. The system also includes an image analysis system to verify a format of the image, verify the lateral flow assay device in the image is authentic, detect a position of the lateral flow assay device in the image, and analyze the image to determine the result of the test by executing a machine learning model.

Example 24 includes the system of Example 23, wherein the image analysis system is remote from the electronic device, and wherein the second instructions cause the electronic device to transmit the image to the image analysis system.

Example 25 includes the system of Example 24, wherein the image analysis system is to transmit the result to the electronic device.

Example 26 includes the system of any of Examples 23-25, wherein the second instructions implement the image analysis system on the electronic device.

Example 27 includes the system of any of Examples 23-26, wherein the machine learning model is a first machine learning model, and wherein the image analysis system is to verify the lateral flow assay device in the image is authentic by executing a second machine learning model.

Example 28 is an image analysis system comprising memory, machine readable instructions, and processor circuitry to at least one of instantiate or execute the machine readable instructions to: (a) determine whether a format of an image of a lateral flow assay device satisfies a format threshold, the lateral flow assay device to implement a diagnostic test to test a sample for a presence or an absence of a target analyte, the lateral flow assay device having a test region to generate a visual indicator representing a result of the diagnostic test, (b) in response to determining the format of the image satisfies the format threshold, determine whether the lateral flow assay device in the image is authentic, (c) in response to determining the lateral flow assay device is authentic, determine whether a position of the lateral flow assay device in the image satisfies a position threshold, (d) in response to determining the position of the lateral flow assay device satisfies the position threshold, analyze the image to determine the result of the diagnostic test, wherein, operations (a)-(d) are performed in sequence, and (e) abort the sequence of the operations (a)-(d) during performance of the sequence of operations (a)-(d) at the time any one of operations (a)-(c) fails.

Example 29 includes the image analysis system of Example 28, wherein the image is obtained by a user electronic device, and wherein the processor circuitry is to: generate an error message upon failure of any one of the operations (a)-(c); and transmit the error message to the electronic device.

Example 30 includes the image analysis system of Examples 28 or 29, wherein the processor circuitry is to determine whether the lateral flow assay device is authentic in operation (b) by executing a first machine learning model.

Example 31 includes the image analysis system of Example 30, wherein the first machine learning model is a Convolutional Neural Network (CNN) model.

Example 32 includes the image analysis system of Examples 30 or 31, wherein the processor circuitry is to analyze the image to determine the result in operation (d) by executing a second machine learning model, the second machine learning model being different than the first machine learning model.

Example 33 includes the image analysis system of Example 32, wherein the second machine learning model is a deep learning model.

Example 34 includes the image analysis system of Examples 32 or 33, wherein the result is a first result, and wherein the processor circuitry is to: analyze the image to determine a second result of the diagnostic test by executing a third machine learning model, compare the first result and the second result, and adjust the first machine learning model based on the comparison.

Example 35 includes the image analysis system of any of Examples 28-34, wherein the processor circuitry is to determine whether the lateral flow assay device is authentic by detecting a target text in the image, the target text including at least one of a brand, a manufacturer, a code, or a type of the lateral flow assay device.

Example 36 includes the image analysis system of any of Examples 28-35, wherein the processor circuitry is to determine whether the lateral flow assay device is authentic by: detecting a machine readable code on the lateral flow assay device, interpreting the machine readable code to obtain a serial number, and comparing the serial number to a list of authentic serial numbers.

Example 37 is at least one non-transitory computer readable medium comprising instructions that, when executed, cause at least one processor to at least: verify a format of an image of a lateral flow assay device, the lateral flow assay device to implement a diagnostic test to test a sample for a presence or an absence of a target analyte, the lateral flow assay device having a test region to generate a visual indicator representing a result of the diagnostic test, verify the lateral flow assay device in the image is authentic, analyze the image using a first machine learning model to determine a first result of the diagnostic test, analyze the image using a second machine learning model to determine a second result of the diagnostic test, the second machine learning model being different than the first machine learning model, compare the first result and the second result, and adjust the first machine learning model based on the comparison.

Example 38 includes the non-transitory computer readable medium of Example 37, wherein the instructions, when executed, cause the at least one processor to flag the first result for manual review by a person if the first result and the second result are different.

Example 39 includes the non-transitory computer readable medium of Examples 37 or 38, wherein the instructions, when executed, cause the at least one processor to analyze the image using the first machine learning model and analyze the image using the second machine learning model in parallel.

Example 40 includes the non-transitory computer readable medium of any Examples 37-39, wherein the first machine learning model is a Convolutional Neural Network (CNN) model.

Example 41 is a system comprising: a server executing first instructions to distribute second instructions to an electronic device including a camera. The second instructions are to guide a user of the electronic device to obtain an image of a lateral flow assay device with the camera. The lateral flow assay device is to perform a test of a sample for a presence or an absence of a target analyte. The lateral flow assay has a test region to generate a visual indicator representing a result of the test. The system also includes an image analysis system to: verify a format of the image of the lateral flow assay device, verify the lateral flow assay device in the image is authentic by executing a first machine learning model, and analyze the image, by executing a second machine learning model, to determine the result of the diagnostic test.

Example 42 includes the system of Example 41, wherein the image analysis system is to: determine an angle of the lateral flow assay device in the image relative to a vertical position, and compare the angle to a threshold range.

Example 43 includes the system of Examples 41 or 42, wherein the image analysis system is to generate an error result if the angle does not satisfy the threshold range.

Example 44 includes the system any of Examples 41-43, wherein at least one of the first machine learning model or the second machine learning model is a Convolutional Neural Network (CNN) model.

Example 45 includes the system of any of Examples 41-44, wherein the second machine learning model is a deep learning model.

Example 46 includes the system of any of Examples 41-45, wherein the result is a first result, and wherein the image analysis system is to analyze the image, using a third machine learning model, to determine a second result of the diagnostic test.

Example 47 includes the system of Example 46, wherein the image analysis system is to compare the first result and the second result and adjust the first machine learning model.

Example 48 includes the system of any of Examples 41-47, wherein the second instructions cause processor circuitry in the electronic device to instantiate the processor circuitry of any of Examples 28-36.

Although certain example systems, methods, apparatus, and articles of manufacture have been disclosed herein, the scope of coverage of this patent is not limited thereto. On the contrary, this patent covers all systems, methods, apparatus, and articles of manufacture fairly falling within the scope of the claims of this patent.

The following claims are hereby incorporated into this Detailed Description by this reference, with each claim standing on its own as a separate embodiment of the present disclosure.

What is claimed is:

1. An image analysis system comprising:
first machine readable instructions;
second machine readable instructions;
a first machine learning model;
a second machine learning model; and
processor circuitry; wherein
the first machine readable instructions, when executed by processor circuitry of an electronic device including a camera and a display, cause the electronic device to:
display one or more user interface screens on the display enabling a user to obtain, using the camera, an image of a lateral flow assay device including a test region for a visual indicator representing a result of a diagnostic test indicative of presence or absence of a target analyte in a sample; and
transmit the image to the processor circuitry of the image analysis system; wherein
the processor circuitry of the image analysis system is remote from the electronic device; and
the second machine readable instructions, when executed by the processor circuitry of the image analysis system, cause the processor circuitry of the image analysis system to:
access the transmitted image;
verify a format of the transmitted image;
identify, from the transmitted image, indicia on the lateral flow assay device indicative of a particular type, a brand, or a serial number of the lateral flow assay device;
determine a first result of the diagnostic test by analyzing the transmitted image using the first machine learning model;
determine a second result of the diagnostic test by analyzing the transmitted image using the second machine learning model;
compare the first result and the second result; and
modify the first machine learning model based on the comparison.

2. The image analysis system of claim 1, wherein the second machine readable instructions, when executed by the processor circuitry of the image analysis system, cause the processor circuitry of the image analysis system to identify the indicia on the lateral flow assay device by executing a third machine learning model.

3. The image analysis system of claim 2, wherein the third machine learning model is a Convolutional Neural Network (CNN) model.

4. The image analysis system of claim 2, wherein the third machine learning model is different than the first machine learning model.

5. The image analysis system of claim 1, wherein the first machine learning model is a deep learning model.

6. The image analysis system of claim 1, wherein the second machine readable instructions, when executed by the processor circuitry of the image analysis system, cause the processor circuitry of the image analysis system to identify, from the transmitted image, the indicia on the lateral flow assay device indicative of a particular type, a brand, or a serial number of the lateral flow assay device by detecting a target text in the transmitted image.

7. The image analysis system of claim 1, wherein the second machine readable instructions, when executed by the processor circuitry of the image analysis system, cause the processor circuitry of the image analysis system to identify, from the transmitted image, the indicia on the lateral flow assay device indicative of a particular type, a brand, or a serial number of the lateral flow assay device by:

- detecting a machine readable code on the lateral flow assay device;
- obtaining the serial number by interpreting the machine readable code; and
- comparing the serial number to a list of authentic serial numbers.

8. The image analysis system of claim 1, wherein the second machine readable instructions, when executed by the processor circuitry of the image analysis system, cause the processor circuitry of the image analysis system to flag the first result for manual review by a person when the first result and the second result are different.

9. The image analysis system of claim 1, wherein the second machine readable instructions, when executed by the processor circuitry of the image analysis system, cause the processor circuitry of the image analysis system to analyze the transmitted image using the first machine learning model and analyze the transmitted image using the second machine learning model in parallel.

* * * * *